US006915227B2

(12) United States Patent
Quimby et al.

(10) Patent No.: US 6,915,227 B2
(45) Date of Patent: Jul. 5, 2005

(54) METHOD OF MATCHING RETENTION TIMES AMONG MULTIPLE CHROMATOGRAPHIC SYSTEM

(75) Inventors: Bruce D. Quimby, Lincoln University, PA (US); Matthew S. Klee, Wilmington, DE (US); Paul C. Dryden, West Chester, PA (US); Elmer A. Axelson, Landemberg, PA (US)

(73) Assignee: Agilent Technologies, Inc., Palo Alto, CA (US)

(*) Notice: Subject to any disclaimer, the term of this patent is extended or adjusted under 35 U.S.C. 154(b) by 0 days.

(21) Appl. No.: 10/722,994

(22) Filed: Nov. 26, 2003

(65) Prior Publication Data

US 2004/0122611 A1 Jun. 24, 2004

Related U.S. Application Data

(62) Division of application No. 09/997,174, filed on Nov. 30, 2001, now Pat. No. 6,691,053.

(51) Int. Cl.[7] ........................ G01D 18/00; G01D 21/00; G01M 19/00; G01P 21/00; G01R 35/00
(52) U.S. Cl. ........................................................ 702/89
(58) Field of Search .................. 702/22, 89; 73/23.35; 703/2; 600/558; 435/6

(56) References Cited

U.S. PATENT DOCUMENTS

| | | | |
|---|---|---|---|
| 3,898,837 A | | 8/1975 | Boege |
| 4,740,903 A | | 4/1988 | Natatsuka et al. |
| 5,205,154 A | * | 4/1993 | Lee et al. .................. 73/23.35 |
| 5,405,432 A | | 4/1995 | Snyder et al. |
| 5,827,946 A | | 10/1998 | Klee et al. |
| 5,958,246 A | | 9/1999 | Tipler et al. |
| 5,987,959 A | | 11/1999 | Klee et al. |
| 6,493,639 B1 | * | 12/2002 | Klee et al. .................... 702/22 |
| 6,544,193 B2 | * | 4/2003 | Abreu ........................ 600/558 |
| 2002/0010566 A1 | * | 1/2002 | Chester et al. ................. 703/2 |
| 2002/0094531 A1 | * | 7/2002 | Zenhausern .................... 435/6 |

FOREIGN PATENT DOCUMENTS

JP          5080041          3/1993

OTHER PUBLICATIONS

Lantos, Janos, et al. Validation of Gas Chromatographic Databases for Qualitative Identification of Active Ingredients of Presticide Residues, pp. 128–137, Oct. 3, 2000.

* cited by examiner

Primary Examiner—John Barlow
Assistant Examiner—Aditya S Bhat

(57) ABSTRACT

A data manipulation method to make local chromatography data more usable and comparable to a reference. The method provides time axis correction to better match local data to a reference of the same time scale, time axis transformation to correspond more directly to a reference based on a different time scale, and response axis correction to better match a reference of the same or different response scale, while maintaining the original peak areas. The method may be used along or concurrently with other data manipulation technique to facilitate operations such as searching, matching, visual comparison, mathematical manipulation, and pattern recognition of chromatographic data.

14 Claims, 35 Drawing Sheets

Delete all peaks not used for RTL2 calibration. Both tables must have same number of peaks.

Master Reference

| # | RT | Compound Name | Area |
|---|------|---------------|---------|
| 1 | 2.138 | methanol | 593.91 |
| 2 | 2.685 | ethanol | 912.34 |
| 3 | 3.081 | acetone | 946.97 |
| 4 | 3.570 | n-pentane | 2681.15 |
| 5 | 5.166 | MTBE | 1300.71 |
| 6 | 6.359 | n-hexane | 2998.45 |
| 7 | 9.652 | n-heptane | 3191.97 |
| 8 | 12.522 | n-octane | 3262.37 |
| 9 | 14.972 | n-nonane | 3351.55 |
| 10 | 17.123 | n-decane | 3368.35 |
| 11 | 19.063 | n-undecane | 3382.36 |
| 12 | 20.844 | n-dodecane | 6926.41 |
| 13 | 22.494 | n-tridecane | 3408.51 |
| 14 | 24.037 | n-tetradecane | 3451.45 |
| 15 | 25.488 | n-pentadecane | 3451.16 |
| 16 | 26.854 | n-hexadecane | 3509.23 |
| 17 | 28.239 | n-heptadecane | 1682.16 |

Local Reference

| # | RT | Area |
|---|------|---------|
| 1 | 2.168 | 95.37 |
| 2 | 2.707 | 151.02 |
| 3 | 3.097 | 178.12 |
| 4 | 3.578 | 351.67 |
| 5 | 5.150 | 207.14 |
| 6 | 6.334 | 394.56 |
| 7 | 9.625 | 420.97 |
| 8 | 12.500 | 431.30 |
| 9 | 14.955 | 440.79 |
| 10 | 17.111 | 444.15 |
| 11 | 19.054 | 448.61 |
| 12 | 20.839 | 917.43 |
| 13 | 22.494 | 454.01 |
| 14 | 24.042 | 466.17 |
| 15 | 25.496 | 464.07 |
| 16 | 26.871 | 471.95 |
| 17 | 28.262 | 229.95 |

Created From: D:\RTL2_PAT\RTL2FID1\530DB1M.D
Comment: master 1x fid 530um cal

Created From: D:\RTL2_PAT\RTL2AED1\DB1MXI2.D
Comment: master 1x aed 530um cal

OK    Cancel

FIG. 14

| # | RT | Compound Name | Area |
|---|---|---|---|
| 1 | 36.000 | n-pentane | 0.00 |
| 2 | 69.000 | n-hexane | 0.00 |
| 3 | 98.000 | n-heptane | 0.00 |
| 4 | 126.000 | n-octane | 0.00 |
| 5 | 151.000 | n-nonane | 0.00 |
| 6 | 174.000 | n-decane | 0.00 |
| 7 | 196.000 | n-undecane | 0.00 |
| 8 | 216.000 | n-dodecane | 0.00 |
| 9 | 235.000 | n-tridecane | 0.00 |
| 10 | 254.000 | n-tetradecane | 0.00 |
| 11 | 271.000 | n-pentadecane | 0.00 |
| 12 | 287.000 | n-hexadecane | 0.00 |

Master Reference

| # | RT | Area |
|---|---|---|
| 1 | 1.200 | 664.46 |
| 2 | 2.117 | 727.41 |
| 3 | 3.210 | 777.22 |
| 4 | 4.167 | 799.69 |
| 5 | 4.985 | 833.21 |
| 6 | 5.704 | 849.97 |
| 7 | 6.352 | 869.99 |
| 8 | 6.949 | 1776.33 |
| 9 | 7.502 | 918.60 |
| 10 | 8.019 | 949.95 |
| 11 | 8.505 | 965.89 |
| 12 | 8.964 | 993.95 |

Local Reference

Delete all peaks not used for RTL2 calibration. Both tables must have same number of peaks.

Created From: manual
Comment: Calibration for converting RT to BP

Created From: G:\RTL2_PAT\RTL2AED3\HC1.D
Comment: calibration for RT -> BP conversion OK    Cancel

FIG. 23

METHOD OF MATCHING RETENTION TIMES AMONG MULTIPLE CHROMATOGRAPHIC SYSTEM

This application is a Divisional of application Ser. No. 09/997,174, filed on Nov. 30, 2001 now U.S. Pat. No. 6,691,053, the entire disclosure of which is incorporated herein by reference.

TECHNICAL FIELD

The technical field generally relates to chromatographic systems and in particular to methods for matching retention times among multiple chromatographic systems.

BACKGROUND

Chromatography (gas, liquid, electro-driven) is a powerful analytical tool that can separate, identify, and quantify multiple analytes in a single analysis. The principal components of a typical chromatographic system include (1) an inlet that provides the interface to transfer a sample mixture into the chromatographic (separation) column; (2) a separation column that separates the sample mixture into its individual components as these components are swept through the column by a mobile phase; (3) a mobile phase to provide a driving force to move solutes from one end of the column to the other, the separation being based on a combination of differential interactions between the components of the sample mixture, an immobilized liquid or solid material within the column (stationary phase) and mobile phase, and (4) a detector that detects and measures components as they exit the separation column at different times. The exit time of a component is defined as the "retention time (RT)" for that component. Some chromatographic methods are capable of separating more than two hundred components in a single analysis. However, for chromatographic methods involving large numbers of components, a significant amount of work is required to determine the RT of each individual component during chromatographic method development. Also significant is the amount of work needed to correlate data generated on multiple instruments performing the same analysis, even for a small number of components.

The problem of replication arises after the chromatographic method development is completed. There are several parameters that affect RT. These include column parameters (e.g., length, stationary phase, particle size, and inside diameter) as well as operating parameters for the chromatograph (e.g., mobile phase type and flow rate, column temperature, ramp rates, column outlet pressure, and stationary phase thickness). Whenever a chromatographic method is used subsequent to its development, it is virtually impossible to replicate all the parameters precisely enough to obtain exactly the same retention times as those observed initially. The cumulative effects of these small but finite differences in parameters usually lead to significant differences in RTs. As an example, when two "identical" gas chromatography (GC) systems were set up to run the same chromatographic method on the same pesticide samples, the RTs for specific solutes were different by 0.5 minutes for peaks eluting at 20 minutes.

Without exact replication, measured RTs do not match the RTs specified in the original chromatographic method or the computerized method files (including calibration and event tables) and can lead to misidentified peaks with grave consequences in applications such as forensic, clinical or environmental analysis. The need therefore exists for means to remove or easily compensate for these RT differences.

Prior Solutions and their Disadvantages

There exist two general ways improving the match of RTs over time and between one system and another: instrumental and calculational. Instrumental approaches seek to reduce differences in RTs by adjusting one or more instrumental parameters such as flow rate and temperature program rate. As a consequence of instrumental approaches, the actual retention times that are generated during analysis more closely match reference RTs.

In calculational approaches, the actual RT data are modified after the RT data are acquired. The most obvious and widely used calculational method for dealing with RT mismatch in a situation subsequent to that of the reference analysis is to re-run a mixture(s) containing all of the possible compounds to be analyzed to determine individual RTs in the new situation. This is a reasonable task for simple chromatographic methods with a small number of well-separated analytes. However, this process becomes much more difficult and time consuming as the number of analytes increases or when using different chromatograph configurations. In addition, this approach does not address the differences between the RTs obtained in a target chromatographic system and those in reference libraries and databases, nor does the approach help in visual or mathematical comparison of chromatographic data obtained on other instruments.

A popular "relative retention" calculational approach utilizes retention indices or Kovats indices that circumvent problems in getting the same retention time from instrument-to-instrument, column-to-column. This type of procedure converts the actual retention times of detected peaks into a number that is normalized to (usually) multiple reference compounds. The Kovats and other relative retention procedures are especially useful for comparing retention times to databases and libraries for identification of individual components. However, these procedures do not help in visual or mathematical comparison of chromatographic data obtained on other instruments, because the procedures adjust the retention times from the integration report and do not effect the plotted chromatographic data or the integrated (slice) data. In addition, most retention index calculations do not use a smoothed correction function, so the resulting indices rely on the accuracy and reproducibility of retention times of reference peaks that bracket the compounds of interest, and are therefore inherently less precise than when using a smoothed correction function.

Lantos et al. describe the application of a polynomial regression to facilitate comparison of retention data from two different GC pesticide databases (Lantos J. et al. "*Validation of gas chromatographic databases for qualitative identification of active ingredients of pesticide residues*" *Principles and Practices of Method Validation* 256:128–137, 2000). Although Lantos et al. had some success at correlating the data, this type of approach is fundamentally flawed. Specifically, the selected data used by the authors came from methods with significant method differences. Changes in stationary phase chemistry, temperatures and flows (outside the rules of method translation) that form the basis of the Lantos approach lead to changes in relative as well as absolute retention times of solutes. General mathematical approaches cannot correct for these changes. Note that in the Lantos reference, the corrected retention times of almost all (18 out of 23) of the peaks selected for listing deviated by more than 1%, with three exceeding 10%. The database searching time windows required for RT differences as high as in Lanto's reference (windows>1 min) would generate a prohibitively high number of hits, rendering the approach unusable. In addition, there is no accommodation for correcting peak response, scaling methods, or changing x-axis or y-axis units in Lanto's method.

An instrumental approach to matching GC retention times is described in U.S. Pat. No. 5,958,246 to Tipler et al. The Tipler technique somewhat improves the match in RTs between systems, but the technique is a very involved, time-consuming procedure and has proven to be limited in practical application.

A more recent and advantageous instrumental approach to solving these problems in GC is that of "retention time locking" (RTL). This technique, described in U.S. Pat. No. 5,987,959 to Klee et al., which is incorporated herein by reference, addresses the problem of matching RTs on multiple systems.

The Klee technique, referred to as the RTL I method hereafter, provides a method for automated matching of retention times obtained using a known chromatographic method having a defined set of column parameters and operating parameters to the retention times obtained using a new chromatographic method having a new set of column parameters, wherein the retention times of components separated in accordance with the new chromatographic method are matched to the retention times set forth in the known chromatographic method. A procedure is described to adjust head pressure to compensate for differences in a new versus the original column, carrier gas, and column outlet pressure of the known chromatographic method.

The use of the RTL I method to enhance identification of unknowns with the use of RT databases is described in U.S. Pat. No. 5,827,946 to Klee et al., which is incorporated herein by reference.

The RTL I method makes significant improvements in the degree to which retention times match between multiple systems and over time. All of the nine tasks listed above and more are improved with the use of the RTL I method. There are, however, shortcomings to the RTL I method. These shortcomings include:

1. While the RT of the locking peak is often very well matched (typically to within 0.005 min), the resolution of pressure adjustment (0.01 psi) is often insufficient to produce a match for the locking peak of better than 0.015 min for columns with inlet pressures below 5 psi. For columns with higher inlet pressures (greater than 20 psi), the match can usually be made to within 0.002 min.
2. Even if the RT of the locking peak is precisely matched, the peaks located at RTs significantly removed from the locking peak can still have significant RT differences from other columns, instruments, libraries, or databases. These differences can be large enough to cause misidentification of compounds and all of the other problems associated with RT differences.
3. In cases where method translation (described in U.S. Pat. No. 5,405,432 to Snyder et al.) is attempted using a column with a different phase ratio than the original one, the current forms of RTL cannot match RTs with as high quality. They deviate by amounts that are not easily predicted or compensated for experimentally.
4. Some analysts use methods with two columns of different types connected to a single injection port but to separate detectors. This approach allows for dual column identification. Only one of these columns can be locked using RTL, however, since there is only one pressure that can be set.

SUMMARY

A method for correlating local chromatographic data to reference chromatographic data, which for convenience will be referred to as the RTL II method, is disclosed. Once a particular chromatographic method (the reference chromatographic method) is developed and validated to satisfaction on a particular chromatographic system (the reference system), a calibration mix of a plurality of calibration compounds with RTs covering the complete RT range of the reference chromatographic method is run. The calibration mix may also provide reference response factors for standard compounds of interest. This process is referred to as the reference calibration, and generates reference calibration data. When a user wants to implement the reference chromatographic method on another chromatographic system (the local system), the user sets up the reference chromatographic method in the local system and preferably, but not necessarily, lock the reference chromatographic method using an instrumental correction technique like the RTL I method. The user then runs the same calibration mix in the local system to create local calibration data. This process is referred to as local calibration. RTL II software uses a mathematical relationship between reference and local calibrations to construct a "local system correction function," which is saved for subsequent use to correct local chromatographic data. In the RTL II process, the peak areas for locally generated chromatographic data are preserved in the corrected local chromatographic data, even though the RTs have been adjusted by the RTL II process to match the reference chromatographic data.

In an embodiment, the RTL II method includes transformation of the time axis of the corrected local chromatographic data into another unit while maintaining the original peak area for accurate quantitation. The transformed axis can possess equally spaced data points (or any other function we choose), even if the relationship between those units and RT is not linear. Examples include time axis transformation to: (1) retention index, which is used extensively in the flavor industry; (2) boiling point, which is used in simulated distillation analysis in the petroleum industry; (3) carbon number, which is of interest to the petroleum industry; (4) molecular weight, which is usually of more of interest in liquid chromatography, and (5) molecular size, which is usually of interest in capillary gel electrophoresis.

In another embodiment, the y-axis of the local chromatographic data is transformed during the transformation procedure. Examples include (1) simple scaling of chromatographic response to remove differences in gain and offset between detectors on different systems; and (2) use of a series of, for example, normal alkanes to correct for systematic variations in response caused by phenomena like molecular weight discrimination in the inlet.

In yet another embodiment, a reference library or database of RTs is transformed so that the reference library or database is now adjusted to more directly correlate to a characteristic of primary interest. Conversely, local chromatographic results can be transformed to better correlate to the reference library or database of chromatographic results.

In yet another embodiment, the construction of the local system correction function and/or the application of this function to the local chromatographic data are performed at a remote site through a network, such as a local network or the Internet.

In summary, the RTL II significantly improves the degree of RT matching and response factor matching beyond that obtained normally or even after using the RTL I (or other instrumental) method. The RTL II method can be used for improving RT matching in all of the situations where the RTL I method can be used, as well as in situations where the RTL I method is not applicable. A number of operations, such as searching, matching, visual comparison, mathematical manipulation, and pattern recognition, will all benefit from the RTL II method.

BRIEF DESCRIPTION OF THE DRAWINGS

The detailed description will refer to the following drawings, in which like numerals refer to like elements, and in which:

FIG. 14 shows an example calibration screen of the RTL II method.

FIG. 23 depicts an example calibration screen for the transformation of x-axis to boiling point.

DETAILED DESCRIPTION

Figure 1A:
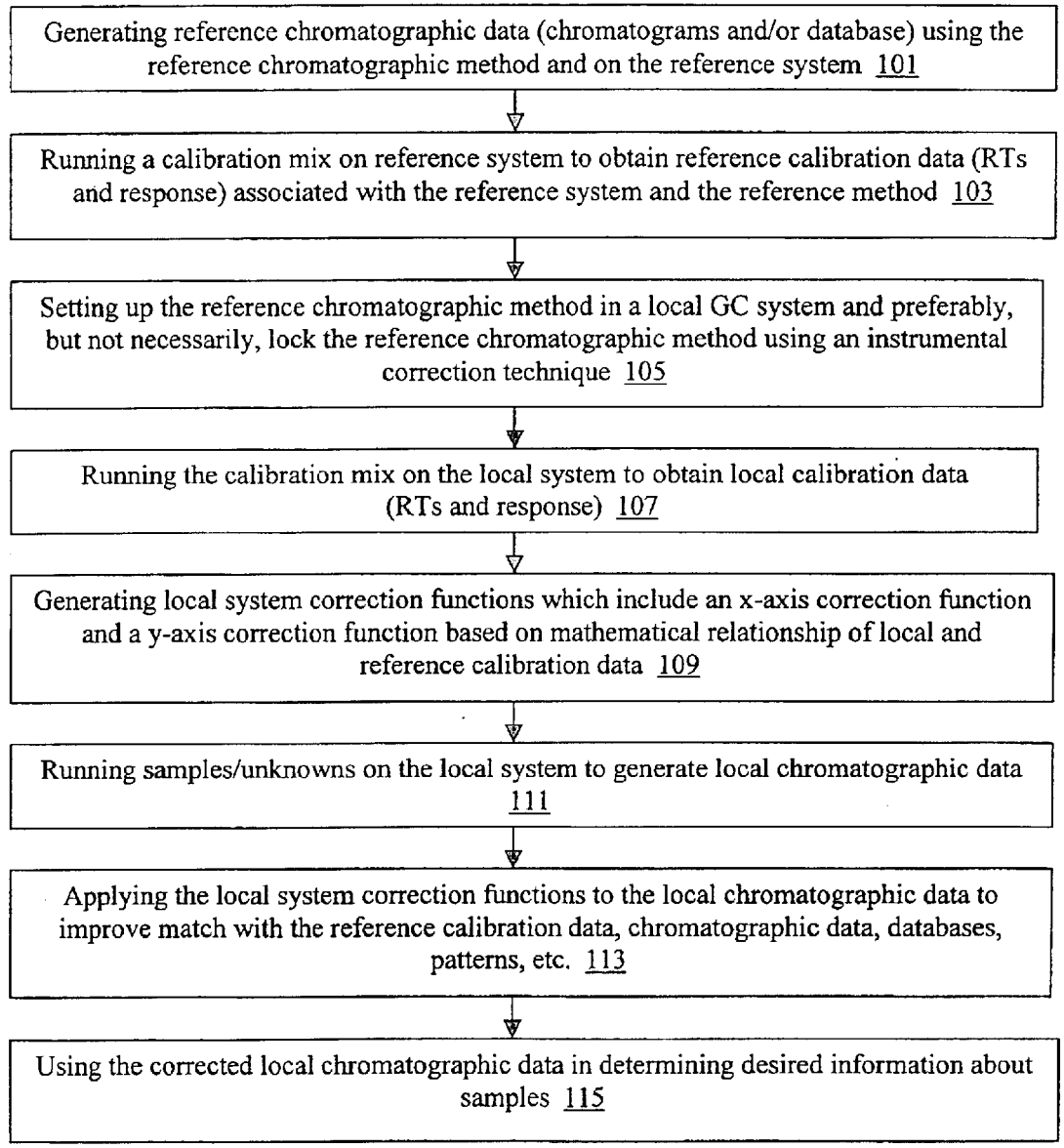
FIG. 1a is a flowchart showing the major steps in the RTL II method.

FIG. 1a depicts the major steps of the RTL II method 100. A reference chromatographic method including all assay parameters, such as column type, mobile phase type or composition, column head pressure or mobile phase flow rate, and temperature program, is developed and validated to satisfaction on a reference chromatographic system. A collection of reference chromatographic data, RTs, responses (chromatograms and/or databases) is then generated using the reference chromatographic method on the reference system (101). A calibration mix of a plurality of calibration compounds with RTs covering the complete RT range of the reference chromatographic method is run on the reference chromatographic system (103). This process is referred to as the reference calibration and generates reference calibration data. The calibration mix should be chosen with consideration of the following guidelines:

(1) The retention times of the calibration compounds should evenly space over the entire retention time range of the reference method.

(2) In the case of irregular instrument conditions, some of the calibration peaks should be chosen to closely bracket the times of discontinuous changes in instrumental parameter such as oven temperature program rate or carrier gas flow rate changes.

(3) The calibration peaks should be at a concentration such that the calibration peaks have sufficient signal response to be easily integrated but are within the capacity limits of the column. Overloading of calibration peaks can degrade quality of the RT matching.

(4) Homologous series (like n-alkanes or methyl esters) make convenient calibration compounds, but any compounds can be used as long as the compounds are chromatographically well behaved.

(5) Calibration compounds should be chosen such that the calibration compounds are similar to the polarity of the samples to be analyzed. In the case of a wide range of polarity in a sample mixture, for example alkanes plus alcohols, compounds in the middle of the polarity range, (like methyl esters in this example), should be chosen.

(6) The concentration of a chosen calibration peak may be adjusted to be different from the concentration of other calibration peaks so that the chosen calibration peak may be more easily identified by subsequent users. In general, a locking peak used for RTL I is often made the tallest peak in the calibration mix. This makes the locking peak easily recognizable both visually and by automated methods.

The calibration mix may also provide reference response factors for standard compounds of interest and for generating response factor correction functions.

When a user wants to implement the reference chromatographic method on another chromatographic system (a local system), the user sets up the reference chromatographic method in a local chromatographic system and preferably, but not necessarily, locks the reference chromatographic method using an instrumental correction technique such as the RTL I method (105). The user then runs the reference calibration mix in the local system to create local calibration data (107). This process is referred to as the local calibration. The RTL II software uses a mathematical relationship between the reference and local calibrations to construct local system correction functions which include an x-axis and a y-axis correction function (109). When a unknown sample is run on the local system using the reference chromatographic method, local chromatographic data is generated (111), the local system correction function is then applied to the local chromatographic data to improve matching between the local chromatographic data and the reference chromatographic data (113). The corrected local chromatographic data is then used to generate desired information such as qualitative identification, quantitative analysis, product integrity decisions, and database storage, for example (115). In the RTL II method, the peak areas of the local chromatographic data are preserved in the corrected local chromatographic data, even though the RTs have been adjusted by the RTL II process to match the reference chromatographic data.

Figure 1B:
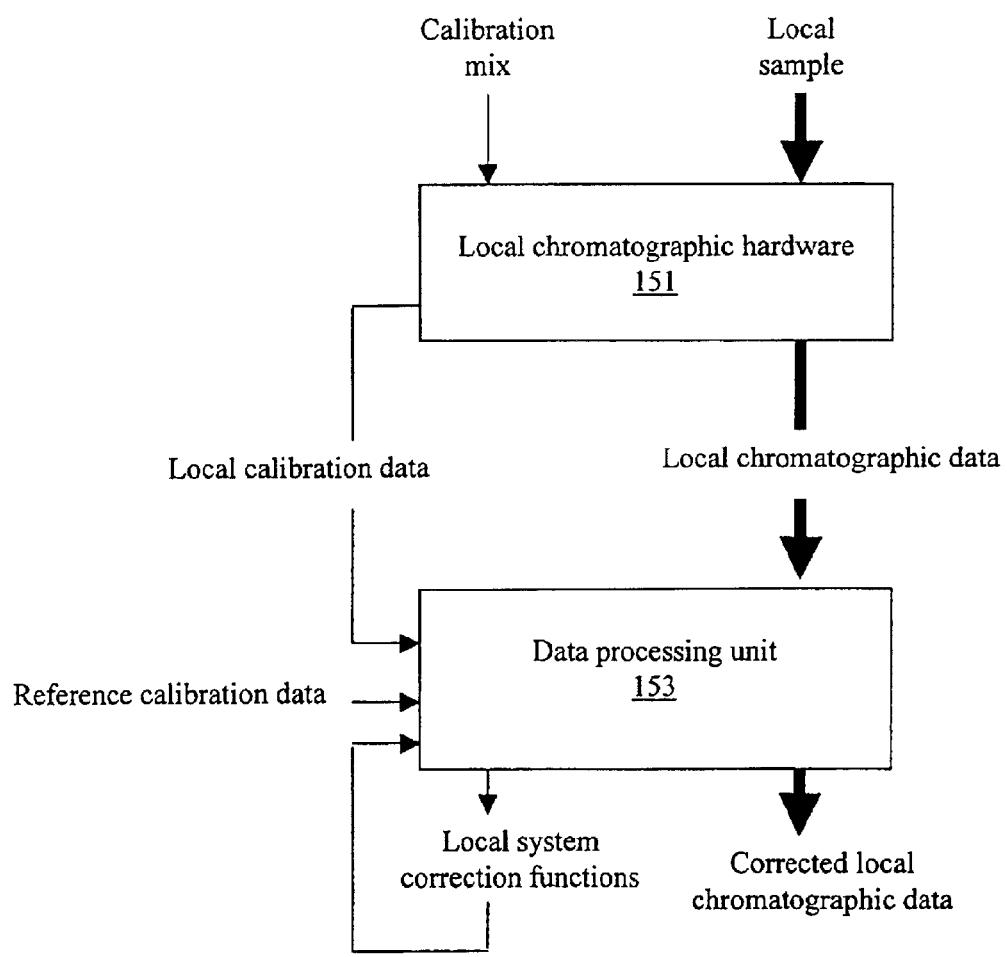
FIG. 1b depicts an local chromatographic apparatus 150 containing the RTL II software.

FIG. 1b depicts a local chromatographic apparatus 150 containing the RTL II algorithms. The local calibration data are produced by the chromatographic hardware 151 and combined with the reference calibration data in data processing unit 153 to generate local system correction functions. The local system correction functions are then stored in the data processing unit 153 and are applied to local chromatographic data to produce the corrected local chromatographic data.

Figure 2:
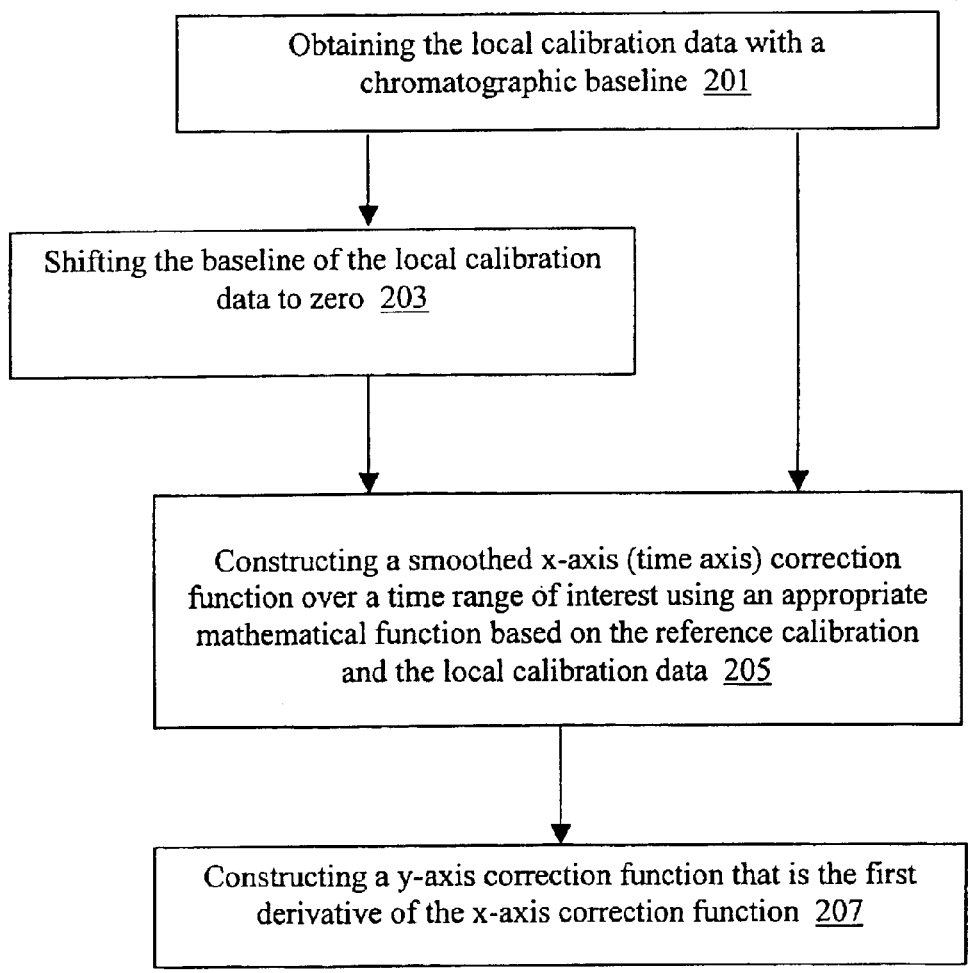
FIG. 2 is a flowchart showing the generation of a local system correction function.

FIG. 2 depicts the construction of the local system correction functions from the local and the reference calibration data (109). The construction process comprises the following steps:

obtaining the reference calibration and the local calibration data (201);

shifting the baseline of the local calibration data to zero to prevent exaggerated baseline drift during response correction (203); this step is optional;

constructing a smoothed x-axis correction function over the time range of interest using an appropriate mathematical function based on a plurality of data pairs from the reference calibration and the local calibration data (205);

constructing a y-axis correction function that is the first derivative of the x-axis correction function (207).

For example, a smoothed correction function can be constructed from RT differences in data pairs of the local calibration and reference calibration data as a function of run time, by using a standard curve fitting algorithm. It may be necessary to extrapolate the local system correction function to extend over a local chromatographic time frame of interest. Higher-order polynomial regressions and cubic splines often fit such data well, although other curve fitting approaches are also effective.

Figure 3:
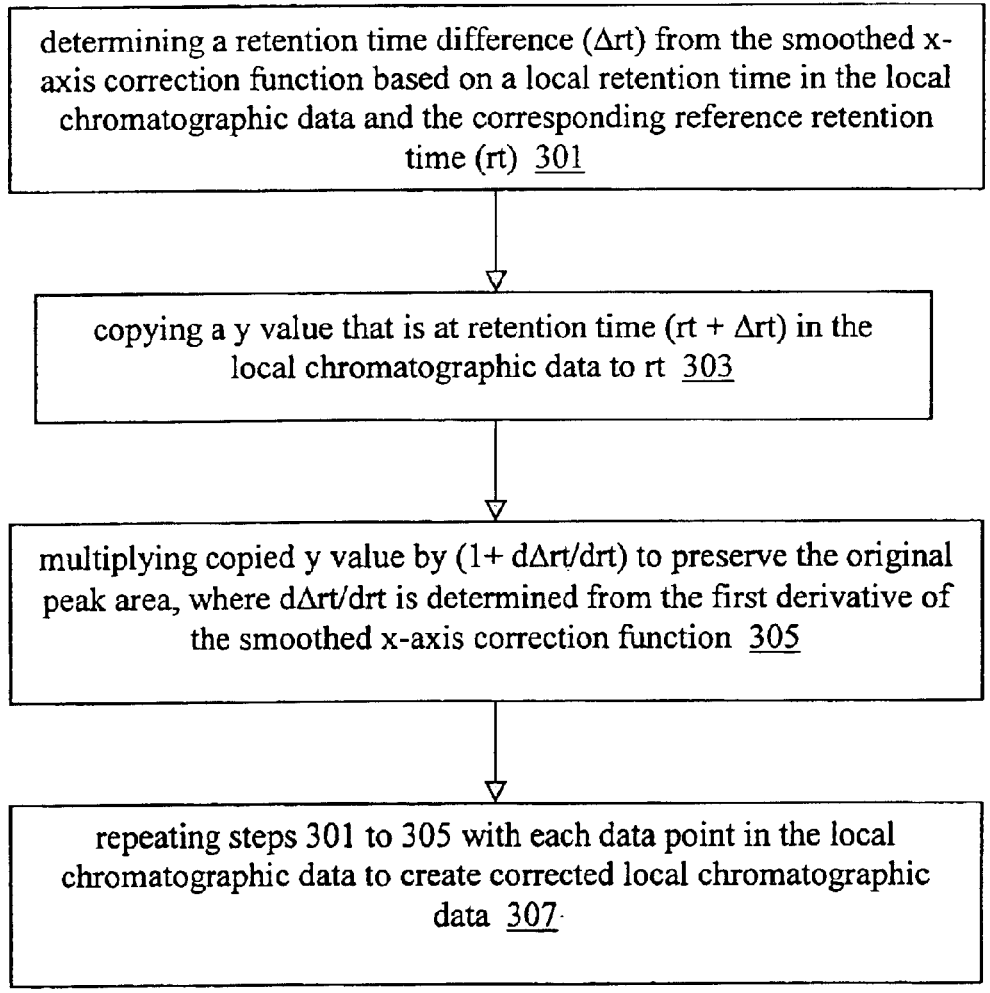
FIG. 3 is a flowchart showing the application of the local system correction function to local chromatographic data.

FIG. 3 depicts the application of the local system correction function to the local chromatographic data in step 113. The application process comprises the following steps:

determining a retention time correction ($\Delta rt$) from the smoothed x-axis correction function of step 205 based on a local retention time (rt) in the local chromatographic data (301);

copying the y value that is at retention time (rt+$\Delta rt$) in the local chromatographic data to rt (303);

multiplying copied y value by (1+d$\Delta rt$/drt) to preserve original peak area, where d$\Delta rt$/drt is determined from a first derivative of the smoothed x-axis correction function (305);

repeating steps 301 to 305 with each data point in the new local chromatographic data to create corrected local chromatographic data (307).

In another embodiment, additional steps are performed before step 205 to simplify the subsequent RTL II process, when the difference in time scales of the reference calibration and local calibration data is large. These additional steps include:

(a) determining a time-axis (retention time) transformation such as a simple linear function, x'=mx+b, which makes the RT of the first and last peaks of the local calibration data match those of the reference calibration data exactly;

(b) applying the time-axis transformation to the local calibration data to create a time-axis transformed local calibration data; and (c) dividing the y value of each time point in the time-axis transformed local calibration data by m (the slope of the simple correction function) to produce transformed local calibration data with corrected local peak areas.

The transformed local calibration data is then used to replace the local calibration data in step 109 to generate a more refined local system correction function.

In this embodiment, the local chromatographic data is also subject to the time-axis transformation and y value correction as described above in step (b) and (c), prior to the application of the local system correction function in step 113.

The RTL II method may be used concurrently with a method translation technique to correct chromatographic data. Method translation is a technique for converting a method to run on (1) columns of other dimensions but having the same type of stationary phase; (2) columns operated at a different speed of analysis; and (3) GC systems of different detector operating pressures. The most important features of method translation is that the method translation maintains the same relative elution order of analytes and yields predictable retention time changes.

Implementation of method translation is described in detail in U.S. Pat. No. 5,405,432 to Snyder et al., which is incorporated herein by reference.

Figure 4:
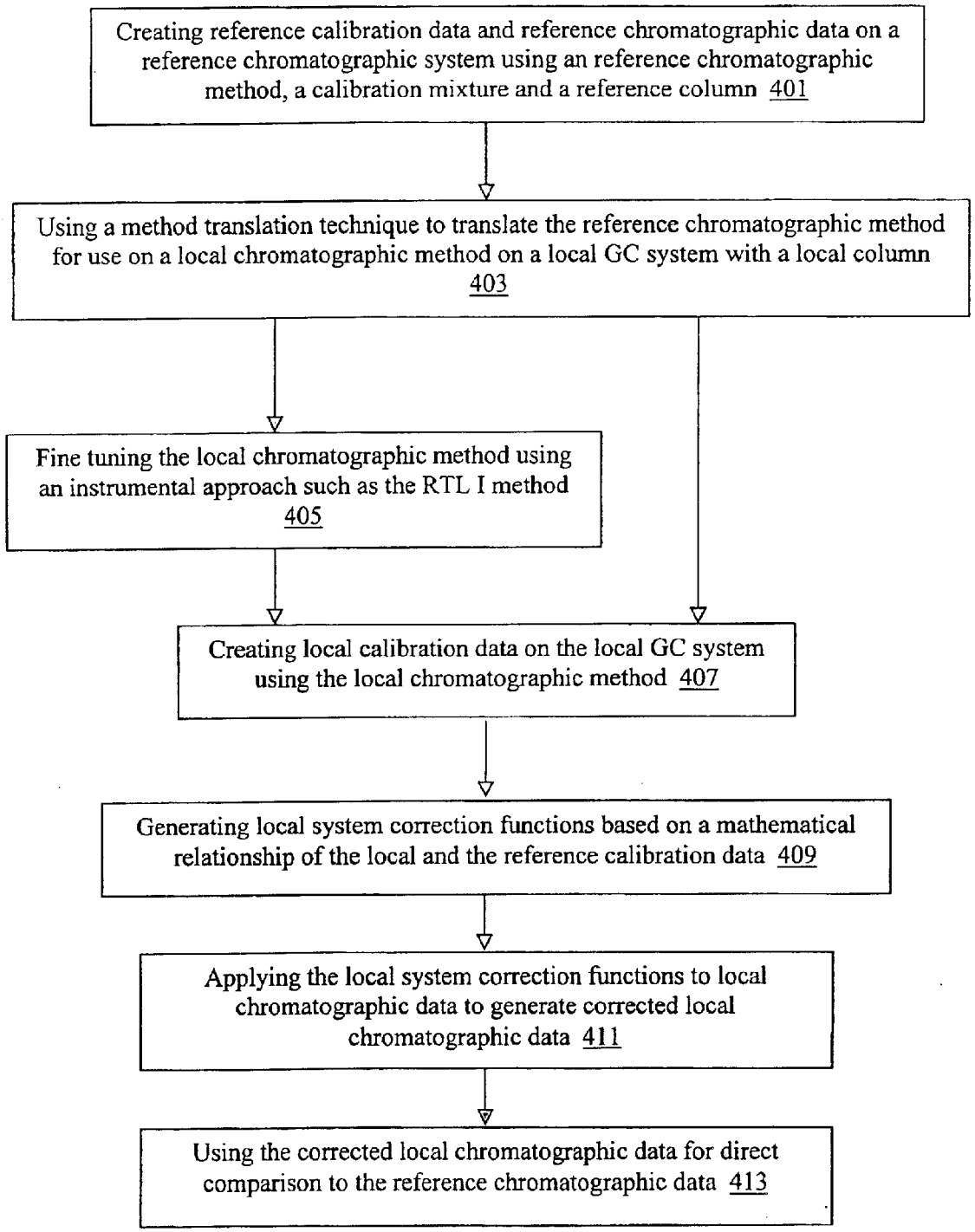
FIG. 4 is a flowchart showing the use of the RTL II method with method translation technique.

FIG. 4 is a flowchart showing the utilization of the RTL II method with the method translation technique. First, reference chromatographic data is created on a reference GC system using a reference chromatographic method and a reference column (401). The reference chromatographic method is then translated into a local chromatographic method by performing the method translation process on a local GC system with a local column (403). An instrumental correction method such as RTL I may be performed (405) prior to the RTL II method to further improve the correlation between the local chromatographic data and the translated reference chromatographic data. Local calibration data is subsequently created on the local GC system using the translated (and perhaps instrumentally corrected) local chromatographic method (407). The local and reference calibration data are used to generate local system correction functions (409). The local system correction functions are then applied to locally generated chromatographic data to produce corrected local chromatographic data (411). When using translated conditions, the corrected local chromatographic data are simultaneously adjusted through the RTL II process to match the reference RTs, greatly facilitating subsequent comparison of the local chromatographic data and the reference chromatographic data (413).

Figure 5:
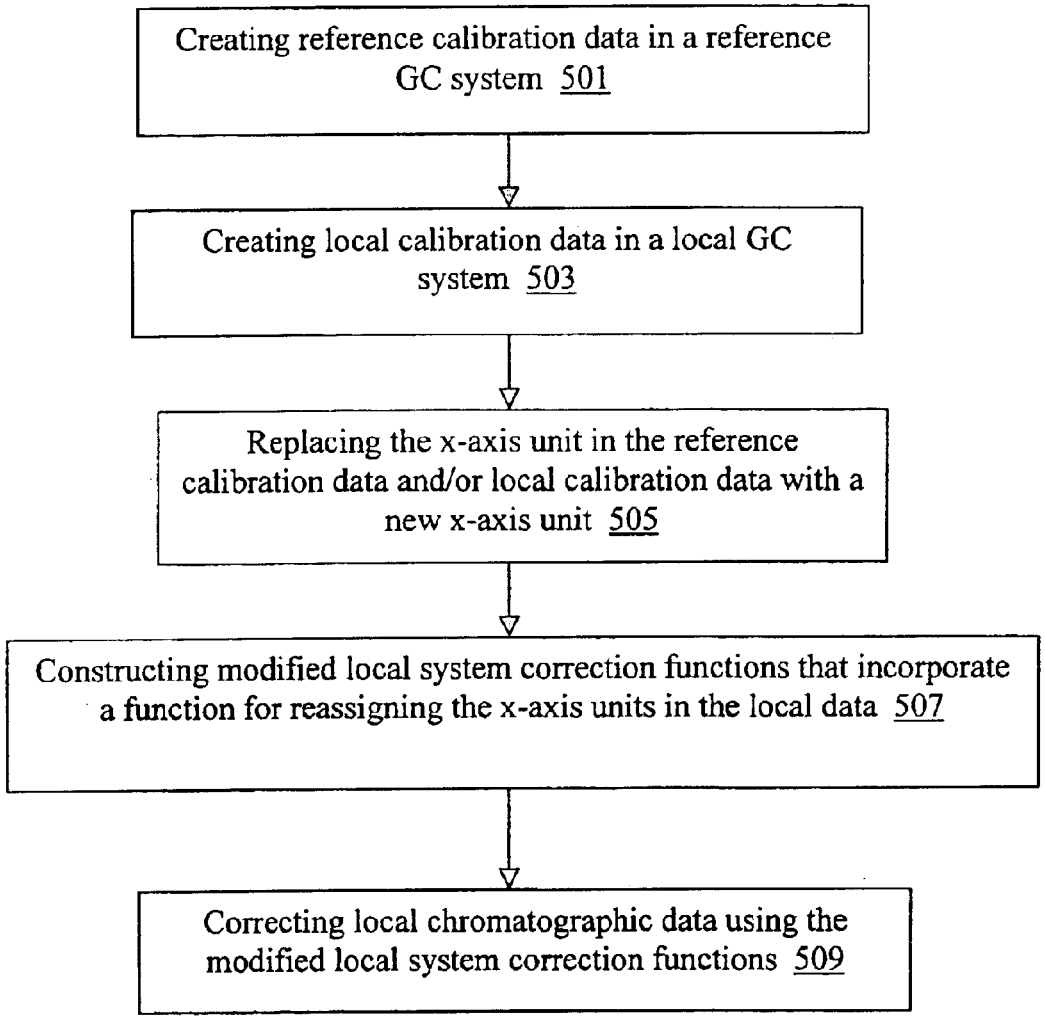
FIG. 5 is a flowchart showing the use of the RTL II method with unit transformation of x-axis.

As shown in FIG. 5, the RTL II method may also include the transformation of the x-axis (RT, migration time, elution volume, etc.) of chromatographic data as required for specific applications, while maintaining the original peak areas. For example, when performing simulated distillation analysis where one replaces RT with boiling point temperature, in capillary gel electrophoresis where one replaces migration time with daltons, and in gel permeation chromatography where one replaces retention time with molecular weight. Reference calibration data and local calibration data are created (501 and 503). A unit transformation is applied by replacing the original x-axis unit of either or both of the reference calibration data and the local calibration data with a new x-axis unit (505). Modified local system correction functions are generated (507) which include a function for reassigning the x-axis units in the local data. The modified local system correction functions are then used to generate corrected local chromatographic data with the new x-axis unit. In another embodiment, the x-axis transformation may be performed as a separate step after the standard RTL II correction process.

Similarly, the y-axis unit can be transformed by replacing an original unit in the reference calibration data and the local calibration data with a new y-axis unit before the construction of the modified local system correction functions. Examples of the new y-axis unit are concentration, percent, weight, mass, moles, and mole fraction.

Better transformation results may be obtained by applying application-specific time transformation functions should the functions be known a priori, instead of empirical functions that are generated based on local calibration data. Examples of such a priori known functions are fundamental principles of chromatography, such as the relationship of flow rate to temperature in GC, or the accepted process of calculating Kovats retention indices using a log function for isothermal conditions and a linear function for temperature programmed conditions. An embodiment that is application-specific is the use of a direct linear relationship to convert the retention time axis to boiling point temperature.

Figure 6:
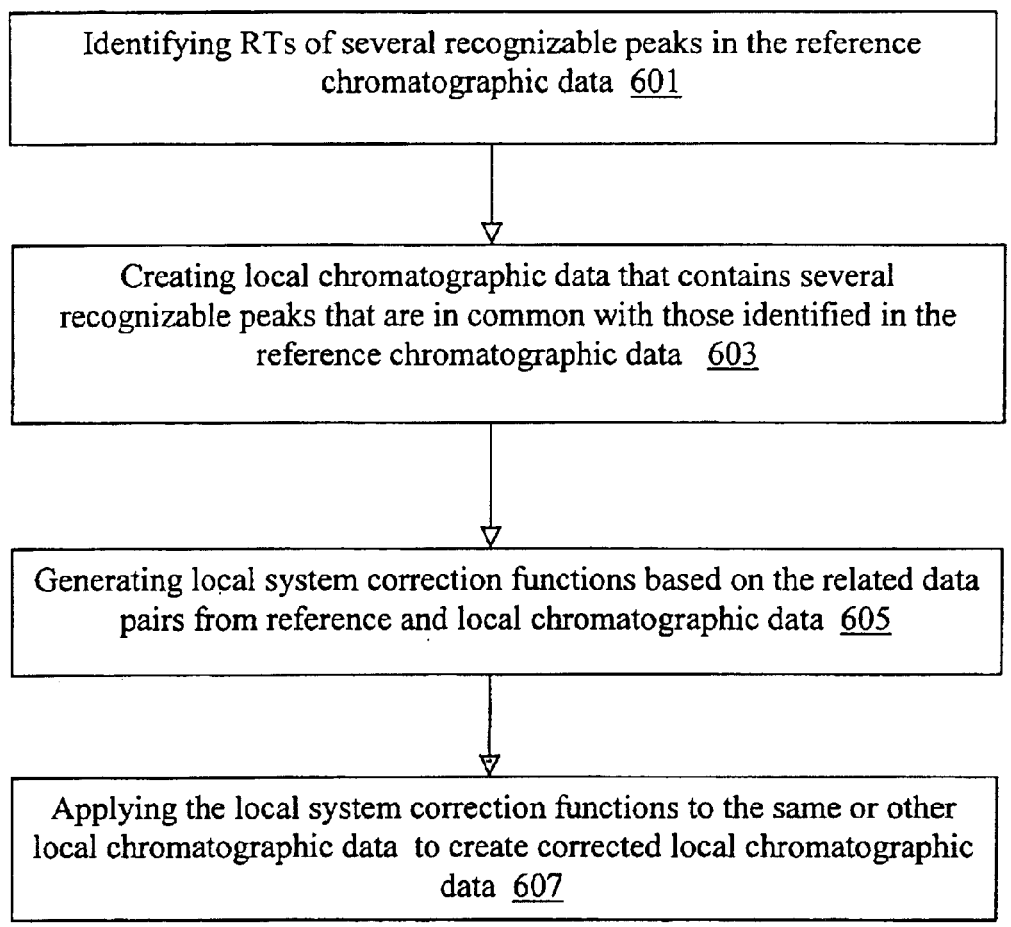
FIG. 6 is a flowchart showing the RTL II transformation of chromatograms without the use of reference calibration mixtures.

The RTL II transformation can also be used to aid in comparison of complex chromatographic data for which no RTL II calibration standards have been run. In an embodiment, peaks found in the chromatographic data itself are used as substitute of the calibration compounds. FIG. 6 depicts an embodiment of a RTL II transformation of chromatograms without the use of reference calibration mixtures. Peaks in a reference chromatographic data are identified by their corresponding RTs (601). Local chromatographic data is then created that contains several recognizable peaks that correspond to those identified in the reference chromatographic data (603). Local system correction functions are created based on the RTs of the corresponding same peaks from the reference and local chromatographic data (605). The local system correction functions are then applied to the same or other local chromatographic data to create corrected local chromatographic data that better correlates to the reference chromatographic data (607).

When comparing chromatographic data either visually or mathematically between chromatographic systems, the RTL II transformation described thus far results in precise matching of the x-axis and maintenance of peak areas. However, there is still a need to match the y-axis in some applications as well. For example, in quality control applications it would be desirable to have multiple chromatographic systems produce precisely the same corrected data when the same sample is run on these chromatographic systems. Having the x and y axes matched enables use of consistent response factors for analyte quantification and facilitates visual inspections for peaks that are too large or small or the appearance of new ones. Chromatographic profiles or fingerprints are more consistent across instruments and system configurations. Pattern recognition, chromatographic data subtraction, and ratioing are also made much easier by y-axis correction.

Figure 7:
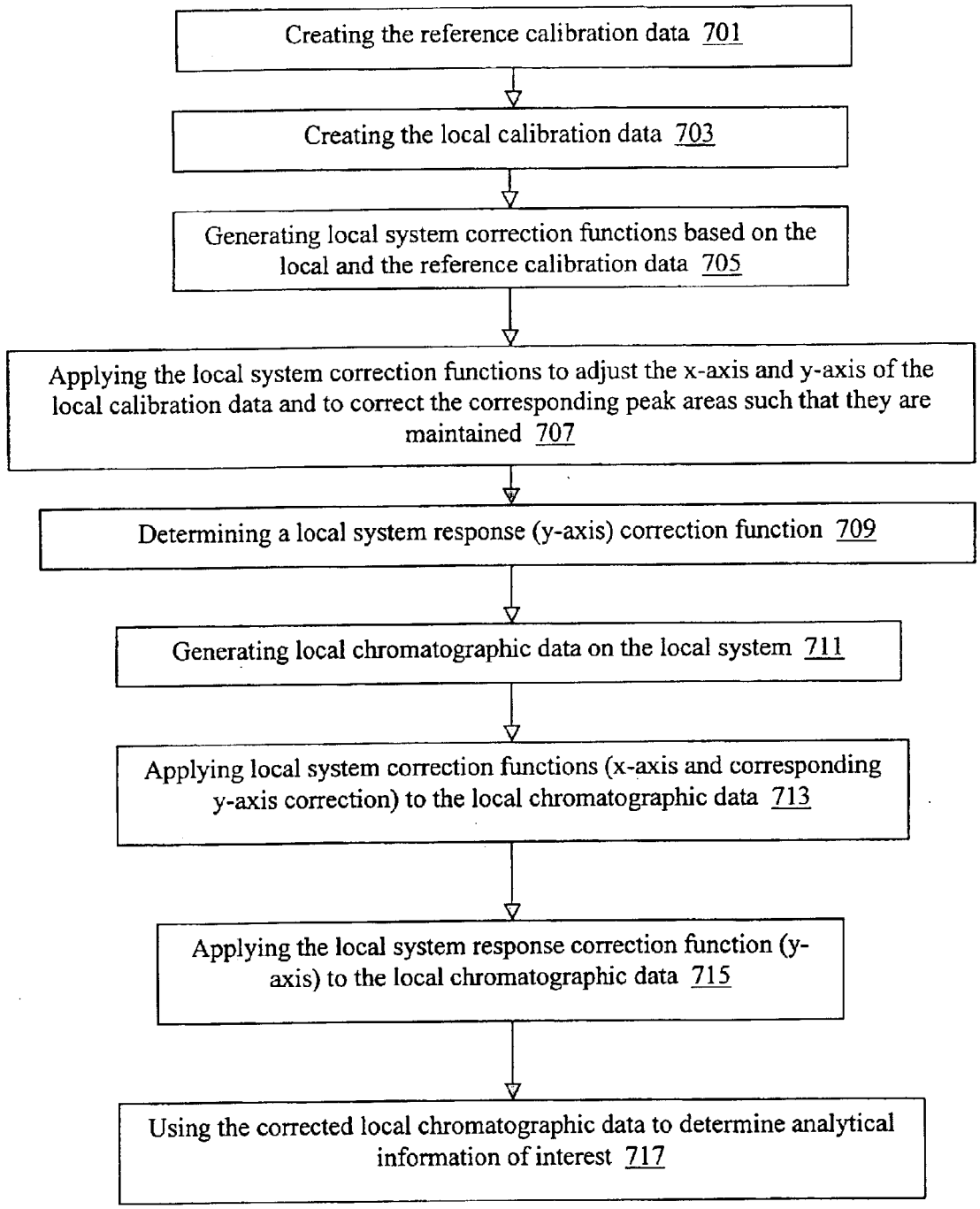
FIG. 7 is a flowchart showing the incorporation of response transformation in the RTL II method.

FIG. 7 depicts an embodiment that combines y-axis transformation with the RTL II method. The embodiment uses a smoothed transformation of the y-axis of the corrected chromatographic data. In this case, a calibration mix that contains the same calibration compounds at the same concentrations is used to create both the reference calibration data (701) and the local calibration data (703). Local system correction functions are generated by a standard RTL II process as described in FIG. 2 and is applied to the local calibration data to adjust the x-axis and to correct the corresponding peak areas (705 and 707). A y-axis local system response correction function is then determined based on the x-axis and area corrected local calibration data and the reference calibration data (709). The y-axis local system response correction function then becomes part of the RTL II transformation method for local chromatographic data (711–717). Applying both the local system correction functions (x-axis and y-axis) and the local system response correction function (y-axis) to local data makes the corrected local data matches that of the reference calibration data better.

The process described above will correct for the differences in peak responses between the local and reference systems. An optional additional step is to offset the entire corrected chromatographic data to have the same baseline level as the reference system.

Figure 34:
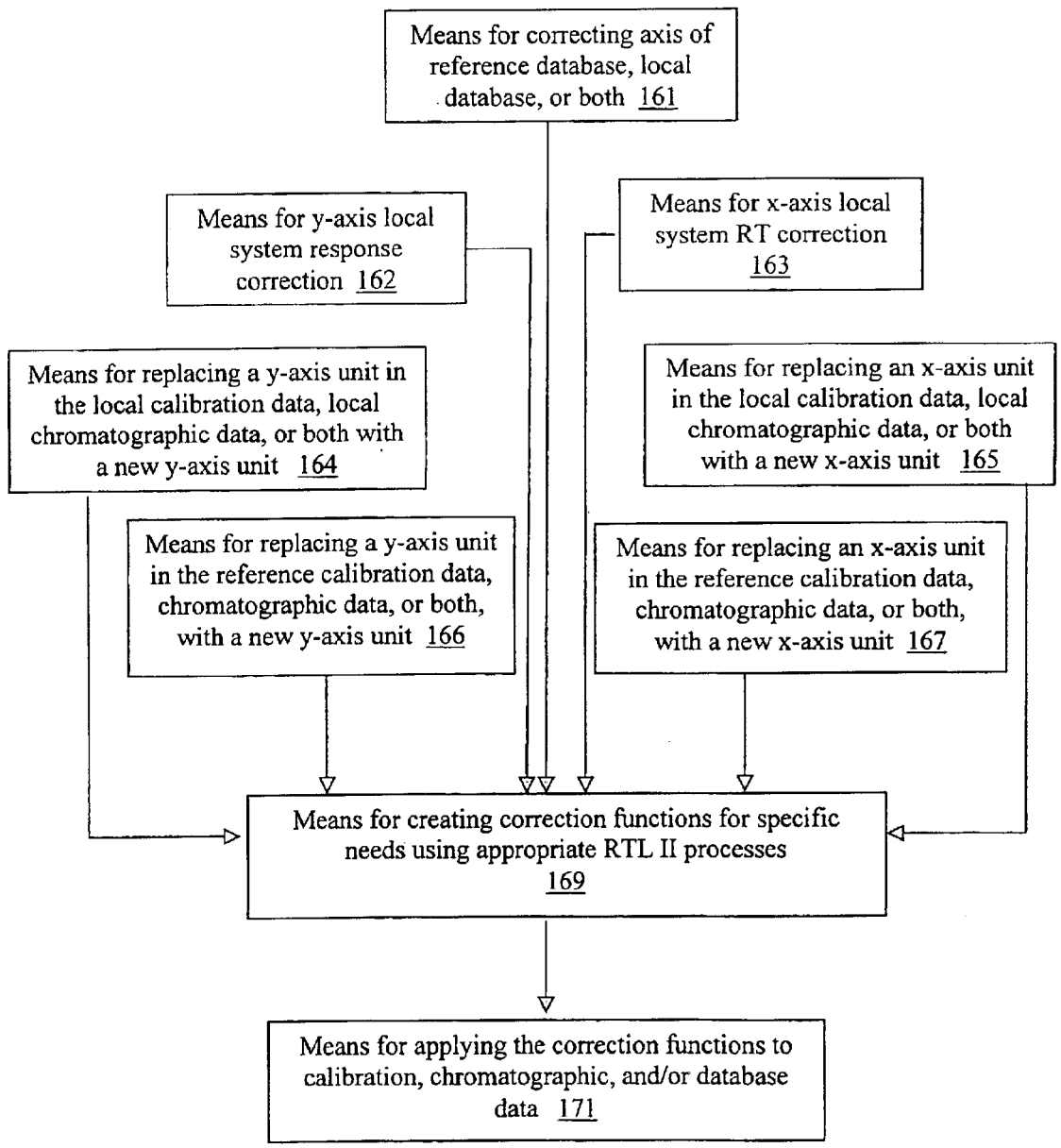
FIG. 34 depicts some capabilities that may be included in the data processing unit 153.

In an embodiment, RTL II method is written as an automated software program such as a ChemStation macro. The local calibration data and local system correction functions are generated and used on the local system. Whenever local chromatographic data is to be corrected, the macro uses the local system correction functions to perform the steps such as described in FIGS. 1–7 on the local chromatographic data in question to match the RTs (and response factors) to the reference system. The ChemStation macro may be stored in the data processing unit 153. FIG. 34 depicts some capabilities that may be included in the data processing unit 153.

The principle behind the RTL II method is to recalculate chromatographic data to make the chromatographic data match a reference. For applications like those described in U.S. Pat. No. 5,827,946 to Klee et al., the goal is to make the RTs from a specific chromatographic setup match precisely those in a library or database. The more closely the RTs match, the smaller the time window that is used to search the database for the identity of an unknown. With smaller time windows, the more likely the search will yield a single result for unknown identification and the more accurate the identification is expected to be. Whenever time windows are wide enough to produce multiple possible identities for an unknown, other analyses are required to finish the identification.

The RTL II method could be used to advantage in this application. The reference calibration data may be the retention times of compounds selected from a database. These same compounds may then be used for the local calibration and the RTL II process.

It is also possible to do the reverse. Instead of recalculating the chromatographic data to match the database, the RTs in the database can be recalculated to match the local system. Sometimes, RT databases have fewer entries than a local analysis has peaks. In these cases, the recalculation is much faster because each local peak is comprised of multiple data points that would otherwise be corrected. However, conversion of the database would need to be performed only once, after which it could be repeatedly used for all library searches done locally.

Figure 8:
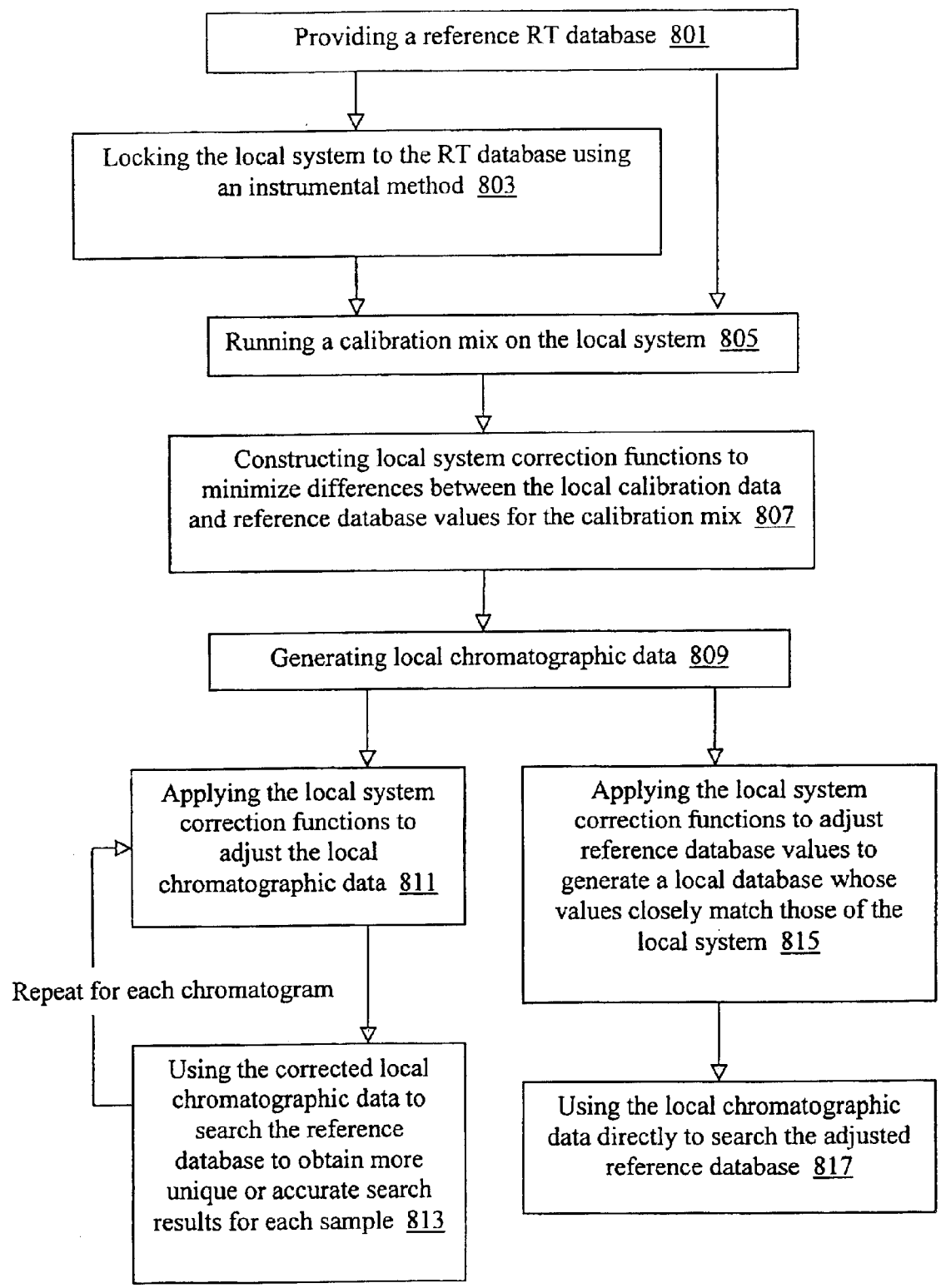
FIG. 8 is a flowchart showing the use of the RTL II method with RT libraries and databases.

FIG. 8 depicts a method to reduce or eliminate the difference in RTs between a local system and a reference database or library. The method comprises the following steps to create corrected local chromatographic data or corrected reference database or library:

providing a RT database (801);

optionally locking the local system to the RT database using an instrumental method such as the method described in U.S. Pat. No. 5,827,946 to Klee et al (803);

running a calibration mix on the local system (805);

constructing local system correction functions to minimize differences between the local calibration data and the reference database values for the calibration mix (807);

generating local chromatographic data (809);

applying the local system correction functions to adjust the local chromatographic data (811);

using the corrected local chromatographic data to search the reference database to obtain more unique or accurate search results for each sample (813).

Steps 811 and 813 may be repeated to correct and search each local chromatogram. Alternatively, the local system correction functions may be applied to the reference database by the following steps:

applying the local system correction functions to adjust the reference database values to generate a local reference database whose values closely match those of the local system (815);

using the local chromatographic data directly to search the local reference database (817).

EXAMPLE 1

Creation of a Reference Calibration

Figure 9:
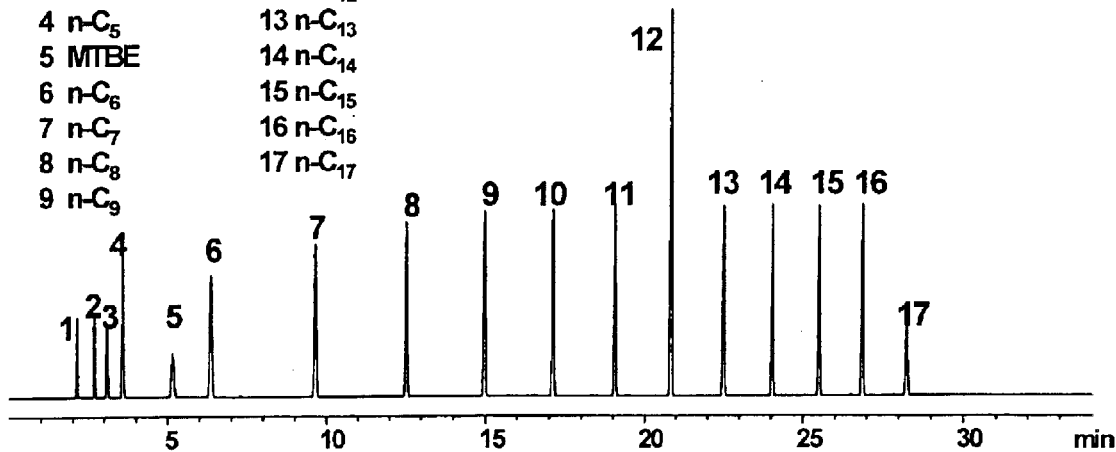
FIG. 9 depicts a reference calibration chromatogram (GC-FID).

A calibration mix was run on a reference GC with a flame ionization detector (GC-FID system) to create a reference calibration. The calibration mix contains four oxygenates and 13 n-alkanes in approximately equal volumes with the exception of n-dodecane, which will be used as the locking peak for RTL. The column characteristics, assay method, and reference chromatogram are shown in FIG. 9.

EXAMPLE 2

Creation of a Local RTL II Calibration

Figure 10:
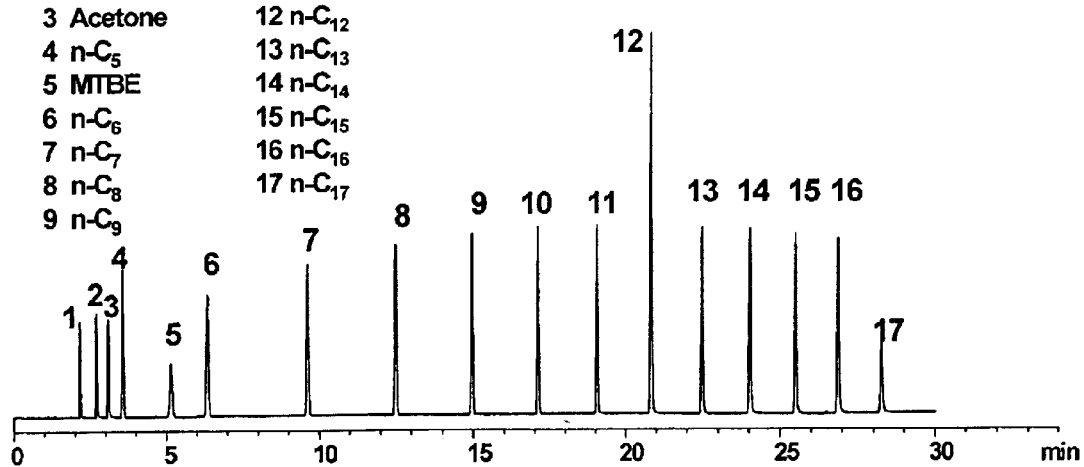
FIG. 10 depicts a local calibration chromatogram (GC-AED).

In this example, the assay method used in Example 1 was duplicated on a local GC system with an atomic emission detector (GC-AED system). The calibration mix was run on the GC-AED system and the dodecane peak was locked using RTL I to be 20.850 min, matching that on the reference GC-FID system. FIG. 10 shows the local calibration data on the GC-AED system.

EXAMPLE 3

Residual RT Differences with RTL

Figure 11:
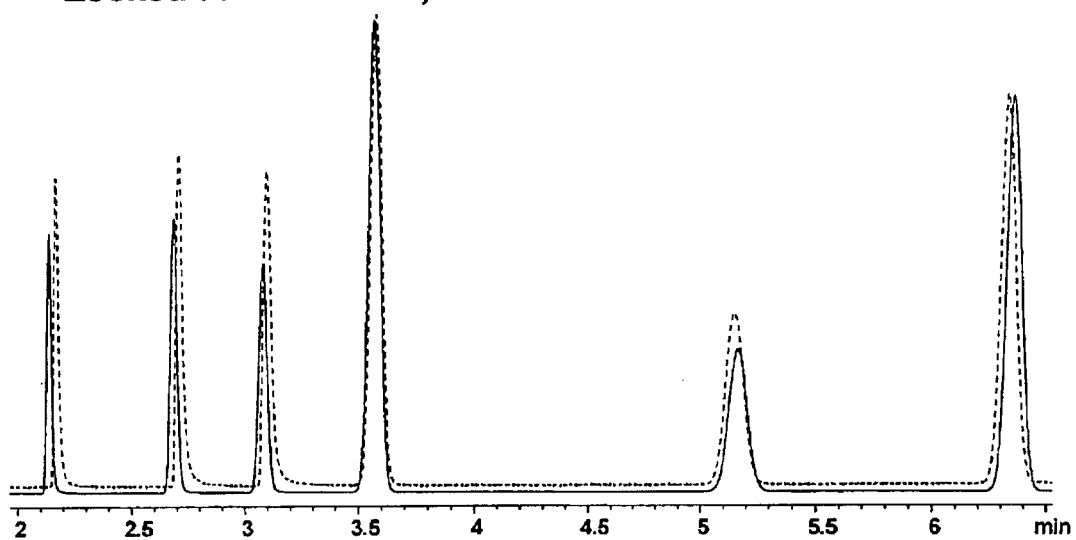
FIG. 11 shows the comparison of early calibration peaks between the GC-FID and GC-AED systems.

This example shows the comparison of early calibration peaks from the reference GC-FID system and the local GC-AED system. FIG. 11 illustrates that, even though RTL locks the n-dodecane peak in both local (GC-AED) the and reference (GC-FID) chromatographic data near 20.850 minutes, there are still residual RT mismatches, especially at the extreme ends of the RT range of 2 to 7 min in this example.

Figure 12:
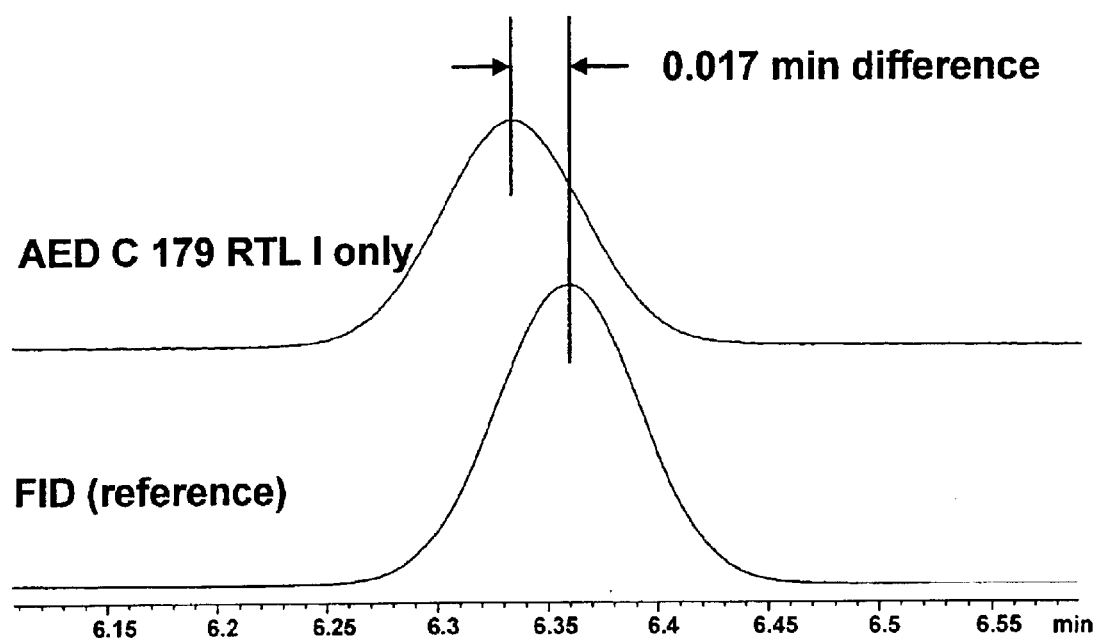
FIG. 12 depicts RTL I residual mismatch in RT for a set of calibration peaks from reference and local calibration chromatograms.

FIG. 12 shows the residual mismatch of the n-hexane peak in more detail near 6.35 min. The difference in measured retention time is 0.017 minutes. This difference is large enough to result in the misidentification of peaks that elute close together. The difference in RT seen in FIG. 12 is what the RTL II method is intended to reduce or eliminate.

Figure 13:
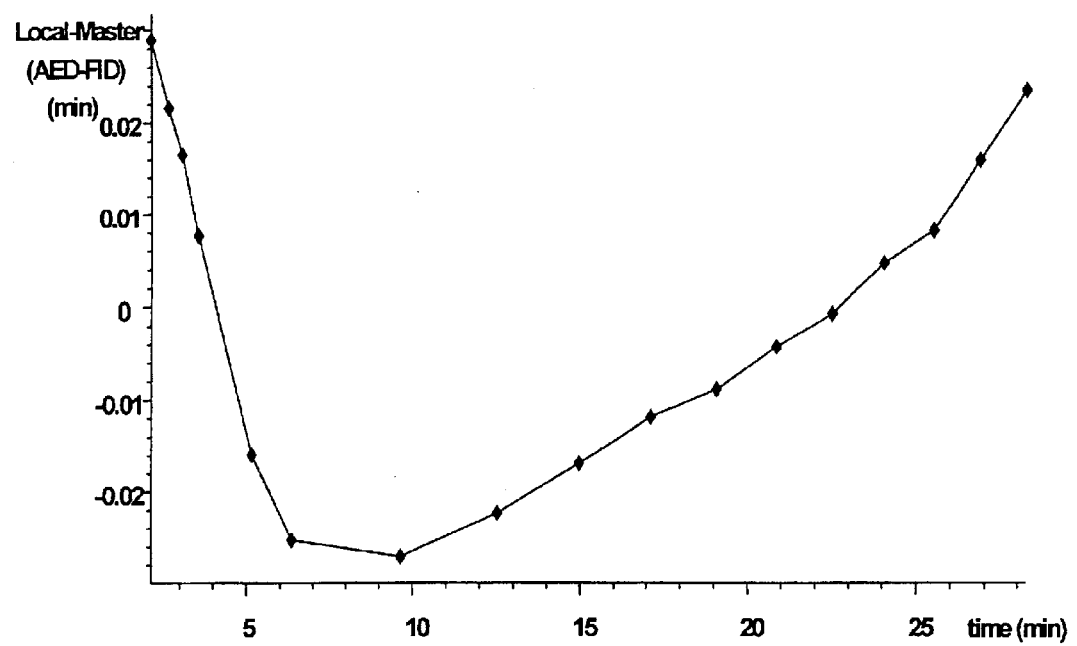
FIG. 13 depicts the difference between calibration peak RTs on the local (AED) and the reference (FID) GC systems vs run time.

FIG. 13 shows a graph of the measured difference in RT for all the calibration peaks between the local (AED) and reference (FID) systems. The differences range from +0.029 minutes to −0.027 minutes.

The shape of the difference curve in FIG. 13 indicates that the largest proportion of the errors is not random in nature, but is the result of some systematic bias. It should therefore be possible to remove a substantial portion of the RT differences between the two systems even for components not in the calibration mix.

EXAMPLE 4

RTL II Transformation of the Local Calibration Data

Figure 15:
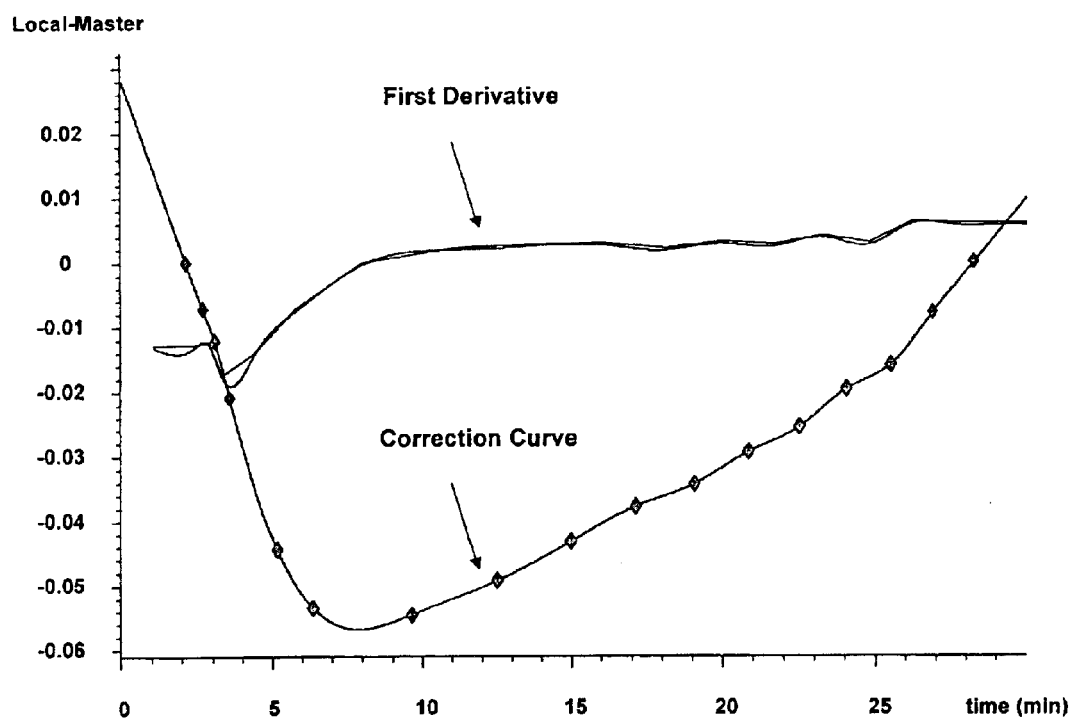
FIG. 15 shows a smoothed difference curve and first derivative curves for the RTL II transformation process.

FIG. 14 shows an example calibration screen from a typical data acquisition and reporting software. The correction function after linear transformation—extrapolation of the ends and curve fitting (e.g., splining in this example)—is shown in FIG. 15. Also shown in FIG. 15 are the first derivative curves, both before and after splining.

Figure 16:
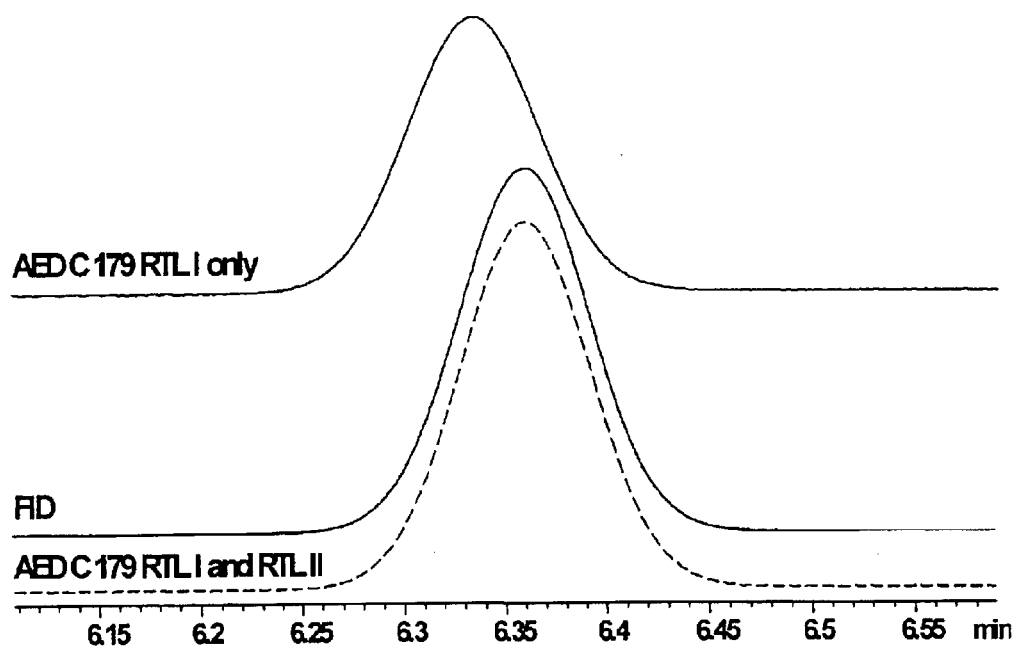
FIG. 16 shows the RT match of calibration chromatograms after employing the instrumental correction of RTL I or RTL I plus RTL II transformation.

FIG. 16 shows the same two chromatograms from FIG. 12 in Example 3 with the corrected version of the local AED calibration added. Note that the retention time now matches much more closely. The agreement of RTs for the calibration mix after RTL I and RTL II is further demonstrated in Table1.

TABLE 1

Agreement of RTs with the RTL I and RTL II method for the calibration mixture

|  | FID RT | AED RTL I | AED RTL II | RTL I Difference | RTI II Difference |
| --- | --- | --- | --- | --- | --- |
| methanol | 2.138 | 2.168 | 2.138 | 0.030 | 0.000 |
| ethanol | 2.685 | 2.707 | 2.685 | 0.022 | 0.000 |
| acetone | 3.081 | 3.097 | 3.081 | 0.017 | 0.001 |
| n-pentane | 3.570 | 3.578 | 3.570 | 0.008 | 0.000 |
| MTBE | 5.166 | 5.150 | 5.166 | -0.016 | 0.000 |
| n-hexane | 6.359 | 6.334 | 6.359 | -0.025 | 0.000 |
| n-heptane | 9.652 | 9.625 | 9.652 | -0.027 | 0.000 |
| n-octane | 12.522 | 12.500 | 12.522 | -0.022 | 0.000 |
| n-nonane | 14.972 | 14.955 | 14.972 | -0.017 | 0.000 |
| n-decane | 17.123 | 17.111 | 17.123 | -0.012 | 0.000 |
| n-undecane | 19.063 | 19.054 | 19.063 | -0.009 | 0.000 |
| n-dodecane | 20.844 | 20.839 | 20.844 | -0.005 | 0.000 |
| n-tridecane | 22.494 | 22.494 | 22.494 | 0.000 | 0.000 |
| n-tetradecane | 24.037 | 24.042 | 24.037 | 0.005 | 0.000 |
| n-pentadecane | 25.488 | 25.496 | 25.488 | 0.008 | 0.000 |
| n-hexadecane | 26.854 | 26.871 | 26.854 | 0.017 | 0.000 |
| n-heptadecane | 28.239 | 28.262 | 28.239 | 0.023 | 0.000 |

EXAMPLE 5

Testing the RTL II Versus RTL I Performance

Figure 17:
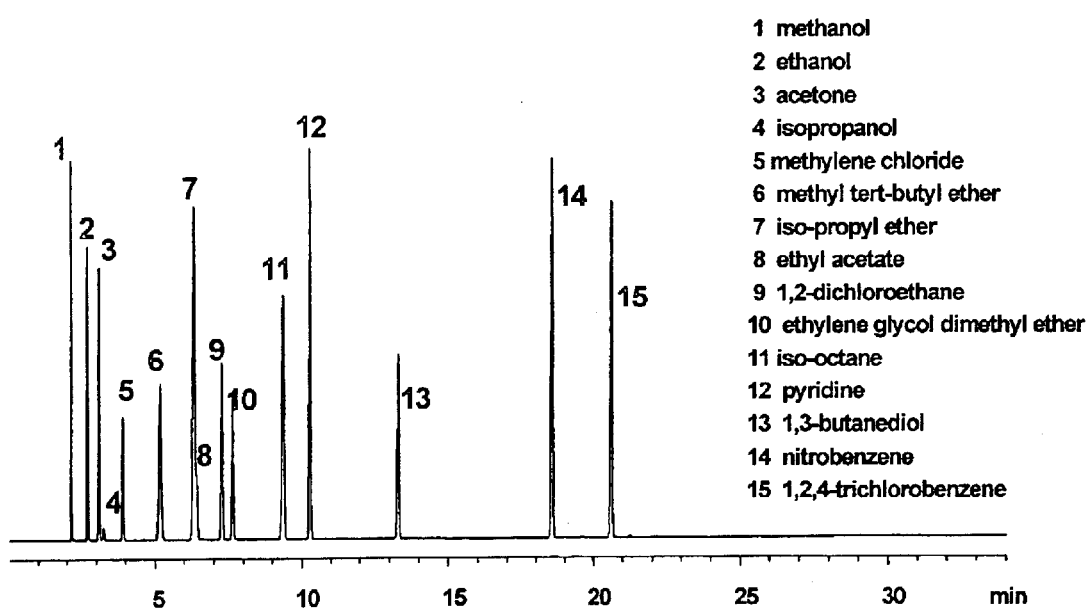
FIG. 17 depicts a chromatogram of the oxygenates mix used to compare the RTL II approach to RT I only.

This example demonstrates the matching effect of RTL II verses RTL I. A test mix containing several oxygenated compounds was run on the GC systems described in Example I using the same assay method. FIG. 17 shows the chromatogram of the test mix run on the local GC system.

The quality of RT matching for the oxygenates mix on the AED local system to the reference FID system with both the RTL I and RTL II processing is compared in Table 2. The RTL II method makes a substantial (tenfold) improvement in RT matching over the RTL I method. The average of the absolute values of the differences between the two systems using the RTL I method is 0.021 minutes. Creating corrected chromatographic data using the RTL H method lowers this average tenfold to 0.002 min.

TABLE 2

Agreement of RTs with the RTL I and RTL II method for oxygenate mixture

|  | AED RTL I | 530 FID (Ref) | AED RTL II | RTL I Difference | RTL II Difference |
| --- | --- | --- | --- | --- | --- |
| methanol | 2.167 | 2.138 | 2.136 | 0.029 | -0.002 |
| ethanol | 2.708 | 2.686 | 2.685 | 0.022 | -0.001 |
| acetone | 3.097 | 3.081 | 3.080 | 0.016 | -0.001 |
| isopropanol | 3.263 | 3.250 | 3.250 | 0.013 | 0.000 |
| methylene chloride | 3.917 | 3.913 | 3.916 | 0.004 | 0.003 |
| methyl tert-butyl ether | 5.150 | 5.165 | 5.166 | -0.015 | 0.001 |
| iso-propyl ether | 6.294 | 6.320 | 6.319 | -0.026 | -0.001 |
| ethyl acetate | 6.392 | 6.416 | 6.418 | -0.024 | 0.002 |
| 1,2-dichloroethane | 7.244 | 7.271 | 7.272 | -0.027 | 0.001 |
| ethylene glycol dimethyl ether | 7.626 | 7.653 | 7.655 | -0.027 | 0.002 |
| iso-octane | 9.323 | 9.354 | 9.351 | -0.031 | -0.003 |
| pyridine | 10.242 | 10.268 | 10.269 | -0.026 | 0.001 |
| 1,3-butanediol | 13.267 | 13.288 | 13.288 | -0.021 | 0.000 |
| nitrobenzene | 18.537 | 18.554 | 18.547 | -0.017 | -0.007 |
| 1,2,4-trichlorobenzene | 20.592 | 20.606 | 20.597 | -0.014 | -0.009 |
| Average (absolute values) |  |  |  | 0.021 | 0.002 |

Figure 18:
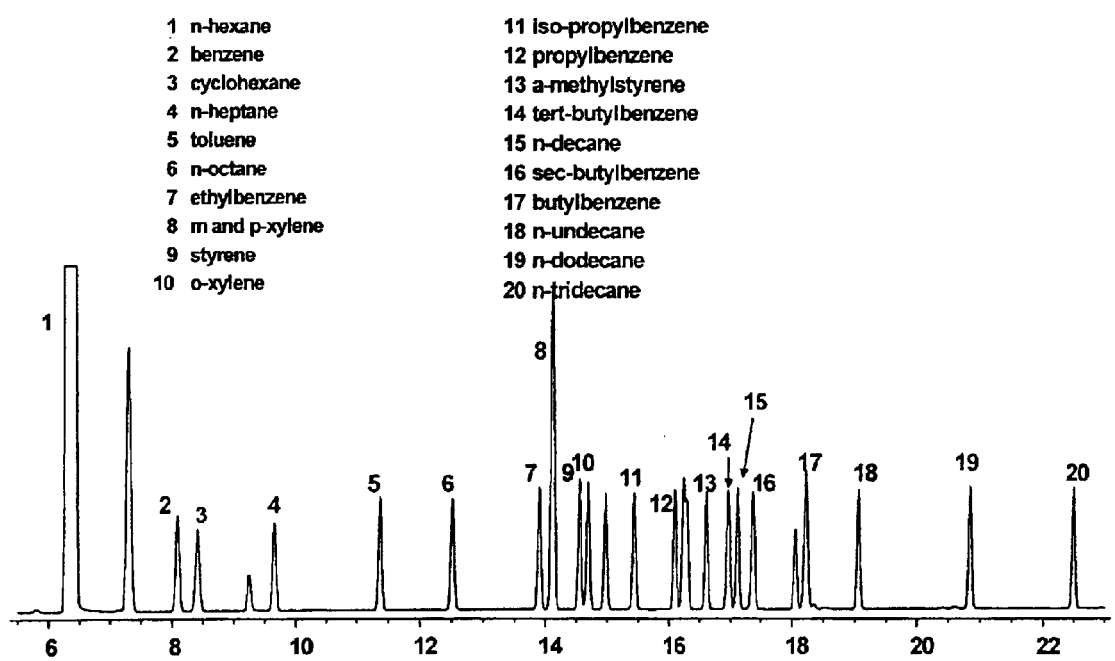
FIG. 18 depicts a chromatogram of the aromatics mix used to compare the RTL II approach to RTL I only.

FIG. 18 shows the chromatogram of another test mixture containing mostly aromatic compounds run on the local GC-AED system of using the same assay method. The results of RT matching for the aromatics mix on the AED local system to the reference FID system with both the RTL I and RTL II method are summarized in Table 3. The RTL II method again makes a substantial (tenfold) improvement in RT matching over the RTL I method. The average of the absolute values of the differences between the two systems using the RTL I method is 0.018 minutes. Creating corrected chromatographic data using the RTL II method lowers this average tenfold to 0.0013 min.

TABLE 3

Agreement of RTs with the RTL I and RTL II method for aromatics mixture

|  | AED RTL I | 530 FID (Ref) | AED RTL II | RTL I Difference | RTL II Difference |
| --- | --- | --- | --- | --- | --- |
| n-hexane | 6.339 | 6.367 | 6.365 | -0.028 | -0.002 |
|  | 7.274 | 7.303 | 7.302 | -0.029 | -0.001 |
| benzene | 8.062 | 8.091 | 8.091 | -0.029 | 0.000 |
| cyclohexane | 8.385 | 8.416 | 8.414 | -0.031 | -0.002 |
|  | 9.216 | 9.245 | 9.244 | -0.029 | -0.001 |
| n-heptane | 9.622 | 9.651 | 9.649 | -0.029 | -0.002 |
| toluene | 11.346 | 11.371 | 11.371 | -0.025 | 0.000 |
| n-octane | 12.497 | 12.520 | 12.519 | -0.023 | -0.001 |
| ethylbenzene | 13.889 | 13.910 | 13.908 | -0.021 | -0.002 |
| m and p-xylene | 14.103 | 14.122 | 14.122 | -0.019 | 0.000 |
| styrene | 14.539 | 14.557 | 14.557 | -0.018 | 0.000 |
| o-xylene | 14.674 | 14.693 | 14.692 | -0.019 | -0.001 |
|  | 14.953 | 14.969 | 14.970 | -0.016 | 0.001 |
| iso-propylbenzene | 15.413 | 15.430 | 15.429 | -0.017 | -0.001 |
| propylbenzene | 16.082 | 16.098 | 16.096 | -0.016 | -0.002 |
|  | 16.227 | 16.242 | 16.241 | -0.015 | -0.001 |
| a-methylstyrene | 16.598 | 16.612 | 16.611 | -0.014 | -0.001 |
| tert-butylbenzene | 16.951 | 16.966 | 16.963 | -0.015 | -0.003 |
| n-decane | 17.110 | 17.121 | 17.122 | -0.011 | 0.001 |
| sec-butylbenzene | 17.348 | 17.361 | 17.360 | -0.013 | -0.001 |
|  | 18.048 | 18.058 | 18.059 | -0.010 | 0.001 |
| butylbenzene | 18.220 | 18.231 | 18.231 | -0.011 | 0.000 |
| n-undecane | 19.053 | 19.060 | 19.062 | -0.007 | 0.002 |
| n-dodecane | 20.838 | 20.839 | 20.842 | -0.001 | 0.003 |
| n-tridecane | 22.494 | 22.491 | 22.495 | 0.003 | 0.004 |
| Average (absolute values) |  |  |  | 0.018 | 0.0013 |

EXAMPLE 6

Using the RTL II Method with Translated Methods: Same Beta

This example demonstrates the use of the RTL II method with the translated method. In this example, the reference system is again the same 530 μm DB-1 system as used in earlier examples. The local system is a GC-FID system with a DB-1 column that is the same length (30 m) but is 250 μm in diameter and with a film thickness of 1.42 μm. Using the method translation technique, a set of conditions were calculated to give the same nominal retention times on the 250 μm column as on the 530 μm column. The 250 μm column was then locked with n-dodecane to elute at 20.850 min. Note that to achieve the same retention times through simple instrumental locking processes link RTL I, it is necessary that ratio of the column diameter to the film thickness is the same (i.e. the same beta) for the two columns, as is the case here.

Figure 19:
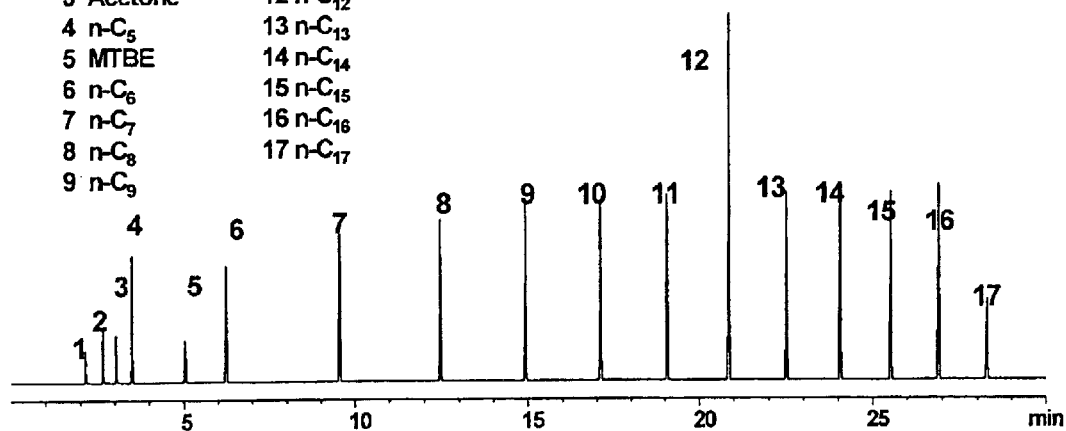
FIG. 19 depicts a local calibration chromatogram on a 250 μm column.
Figure 20:
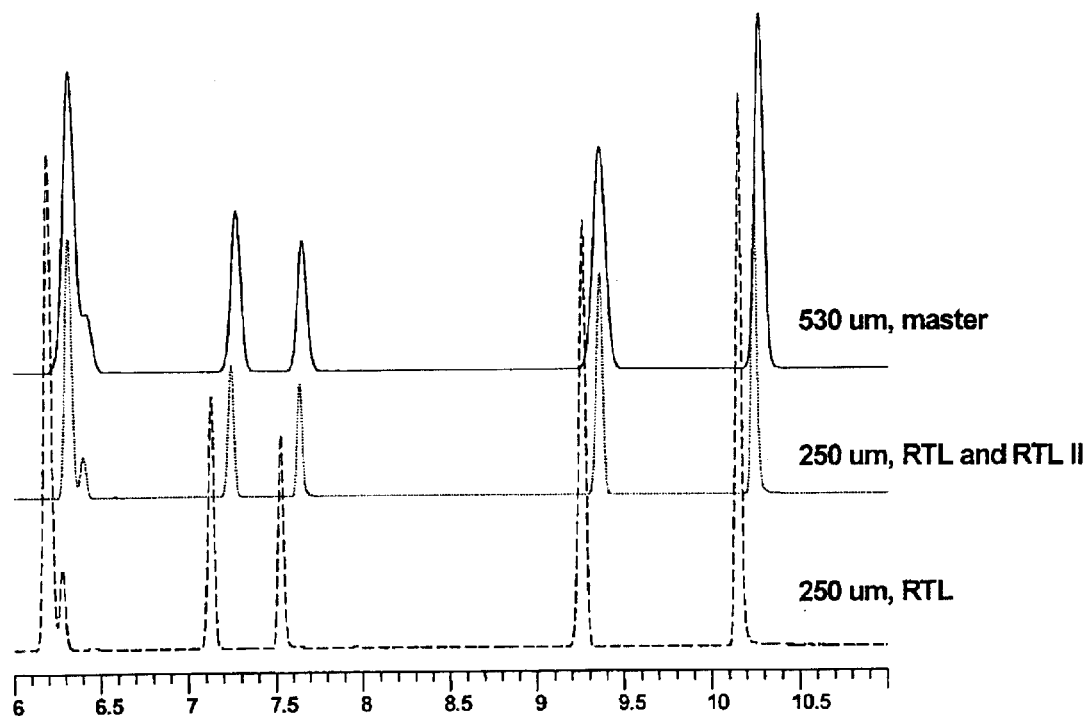
FIG. 20 shows the RT matching of the oxygenates mix on 530 μm and 250 μm columns with same column diameter to film thickness ratio (beta) using the RTL II vs the RTL I method.

FIG. 19 shows the local calibration chromatogram on the 250 μm column. The reference calibration chromatogram is shown in FIG. 9. The oxygenates test mixture was then used to evaluate the quality of RT matching with both the RTL I and RTL II method. FIG. 20 and Table 4 below shows the improvement in RT matching provided by the RTL II method. As seen in Table 4, the improvement in RT matching with the RTL II method is significant. The differences in RTs are reduced on average fivefold.

TABLE 4

Agreement of oxygenate mix RTs with the RTL I and RTL II method for columns of different diameter but same beta

|  | 250 RTL I | 530 FID | 250 RTL II | RTL I Errors | RTL II Errors |
|---|---|---|---|---|---|
| methanol | 2.133 | 2.138 | 2.132 | −0.005 | −0.006 |
| ethanol | 2.656 | 2.686 | 2.684 | −0.030 | −0.002 |
| acetone | 3.034 | 3.081 | 3.080 | −0.047 | −0.001 |
| isopropanol | 3.196 | 3.250 | 3.247 | −0.054 | −0.001 |
| methylene chloride | 3.829 | 3.913 | 3.901 | −0.084 | −0.012 |
| methyl tert-butyl ether | 5.047 | 5.165 | 5.167 | −0.118 | 0.002 |
| iso-propyl ether | 6.194 | 6.320 | 6.315 | −0.126 | −0.005 |
| ethyl acetate | 6.281 | 6.416 | 6.402 | −0.135 | −0.014 |
| 1,2-dichloroethane | 7.128 | 7.271 | 7.243 | −0.143 | −0.028 |
| ethylene glycol dimethyl ether | 7.526 | 7.653 | 7.638 | −0.127 | −0.015 |
| iso-octane | 9.256 | 9.354 | 9.356 | −0.098 | 0.002 |
| pyridine | 10.149 | 10.268 | 10.240 | −0.119 | −0.028 |
| 1,3-butanediol | 13.200 | 13.288 | 13.255 | −0.088 | −0.033 |
| nitrobenzene | 18.494 | 18.554 | 18.503 | −0.060 | −0.051 |
| 1,2,4-trichlorobenzene | 20.563 | 20.606 | 20.557 | −0.043 | −0.049 |
|  | Average (absolute values) |  |  | 0.085 | 0.017 |

EXAMPLE 7

Using the RTL II Method with Translated Methods: Mismatched Beta

A more difficult application of the RTL II method is the situation where the method is translated to a column with a different beta. In this example, the experiment described in Example 6 was repeated using a 250 μm DB-1 column as above except with a film thickness of 1.00 μm instead of 1.42 μm. This 40% mismatch in beta means that the RTL I method cannot be used effectively, because adjusting the inlet pressure to make the n-dodecane locking peaks match would change the flow so much as to potentially change the elution order of some peaks. Therefore, this is an example of where the RTL II method can be used to unique advantage.

Figure 21:
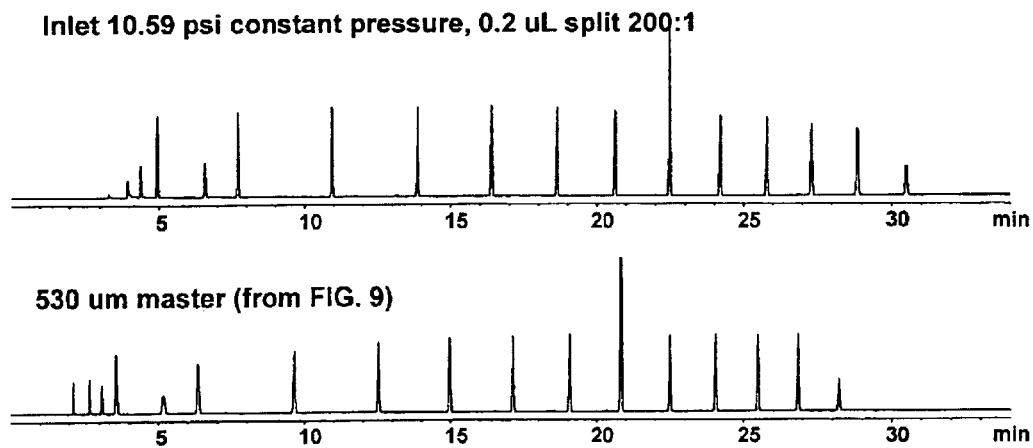
FIG. 21 shows the calibration chromatograms for the 530 μm reference column (lower trace) and the 250 μm local column with mismatched beta (upper trace).

The reference is again the 530 μm column whose calibration is shown in FIG. 19 FIG. 21 shows the two calibration chromatograms. The 250 μm (local) calibration is the upper trace and the 530 μm reference (from FIG. 9) is the lower. Use of the RTL II method reduced the time difference for the oxygenates mixture to an average of 0.011 minutes and for the aromatics to an average of 0.010 minutes. This is a greater than 100 fold reduction in the RT differences compared to that shown in FIG. 21.

Please note that the differences in RTs from the local to the reference are so large in this example that the peak areas change substantially in the corrected chromatographic data if the response corrections discussed earlier (and in FIGS. 3 and 7) are not used. The change in area was as large as 20% without using the first derivative correction. Incorporating the first derivative correction dropped the measured change in area to below the experimental error in integrating the peaks (~1%).

EXAMPLE 8

Transformation of X-Axis to other Units

Figure 22:
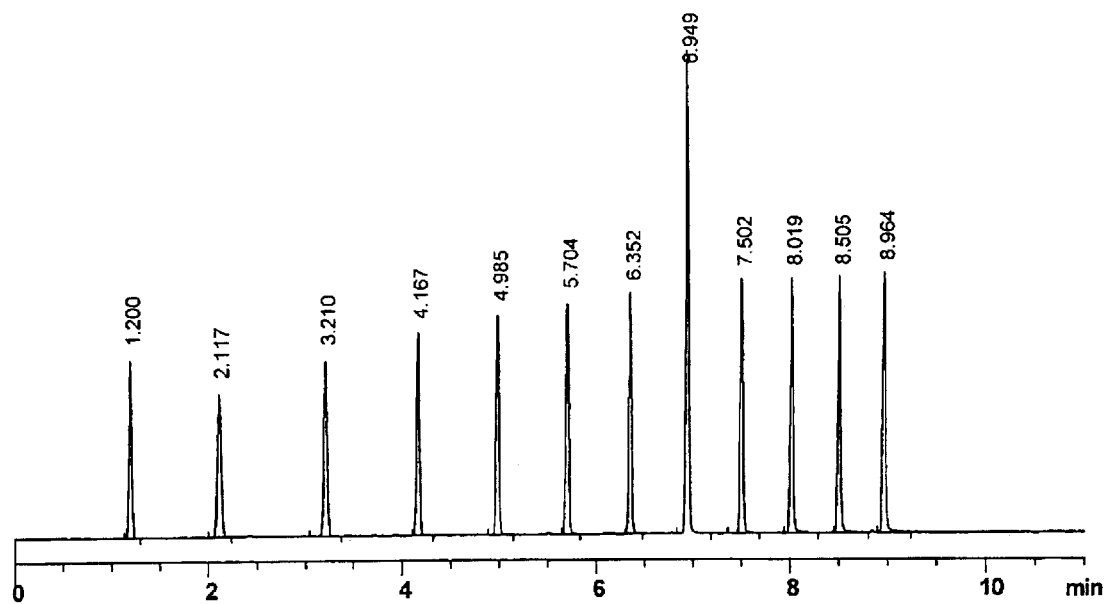
FIG. 22 depicts the reference calibration chromatograms for the 530 μm reference GC column used for calibration of boiling point.

This example shows the transformation of x-axis units by the RTL II method. FIG. 22 is a chromatogram of a mixture of n-C5 through n-C16 alkanes run on GC-AED. The peaks are labeled with RTs determined by a ChemStation integrator. To convert chromatographic data run on this system to a boiling point x-axis, the retention times in the reference calibration are replaced with the boiling points (in this example ° C.) of each alkane.

An example RTL II calibration screen for converting to boiling point on the x-axis is shown in FIG. 23. The reference retention times had previously been replaced in this screen by the boiling points.

Figure 24:
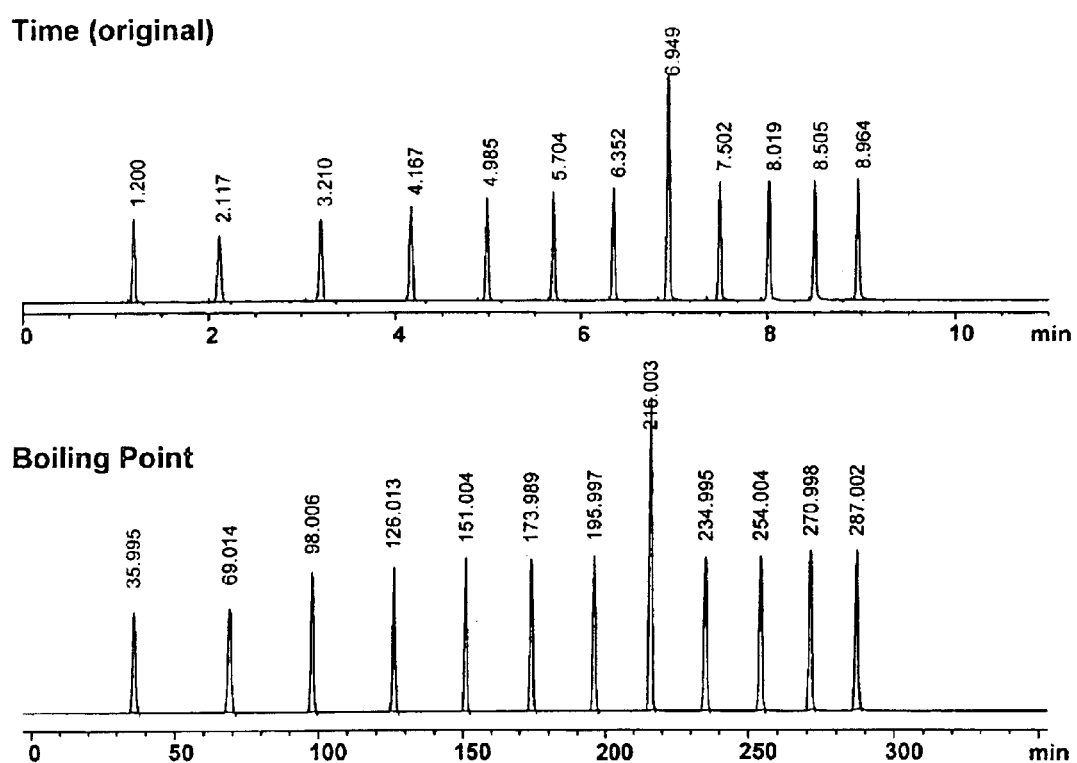
FIG. 24 shows the conversion of x-axis unit from time to boiling point with the RTL II method.

FIG. 24 shows the corrected chromatographic data of the same alkanes before and after transformation to boiling point. One handy feature of the process is that the ChemStation integrator now labels peaks with temperature. This type of display should be useful to petroleum refiners because they can easily read the boiling point of a compound directly from the corrected chromatographic results.

Other conversions that may be performed with this approach include retention index and molecular weight. Note that in some retention index calculations, log interpolation is used during isothermal sections of the chromatogram and linear interpolation during the temperature programming. This approach can be used in the calculation of corrected chromatographic data as an option, but corrections in the transition zones from one algorithm to the other become less accurate because they are more difficult to curve fit.

EXAMPLE 9

Transformation of Chromatographic Data without Calibration Data

The RTL II calculation can be used to aid in comparison of complex chromatographic data for which no calibrations have been run. This example shows the comparison of two chromatograms of orange oil run on two different columns using the RTL II method. The columns are of different diameters, 320 and 530 μm. The 530 μm GC conditions were calculated using the method translation to yield runs that were two times faster than with the 320 μm column.

The reference calibration was created by entering the retention times of several recognizable (although unknown) peaks in the 320 μm chromatogram and then entering the corresponding RTs of the same peaks from the 530 column for the local calibration.

Figure 25:
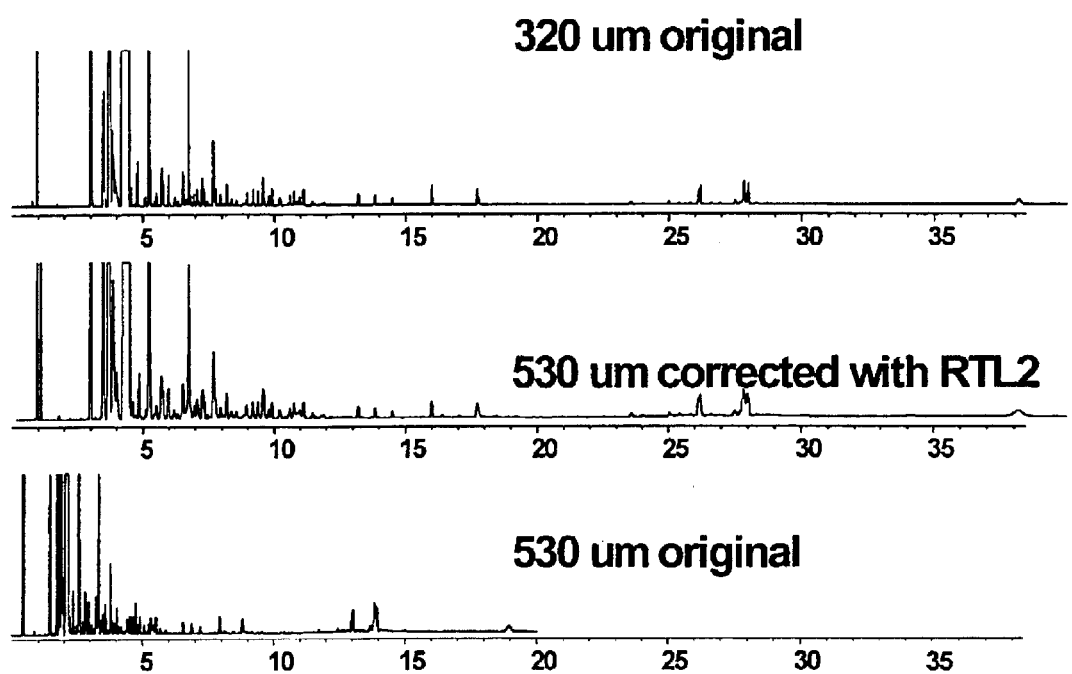
FIG. 25 depicts an orange oil chromatogram corrected using the RTL II method and calibration with (unknown) peaks present in sample.
Figure 26:
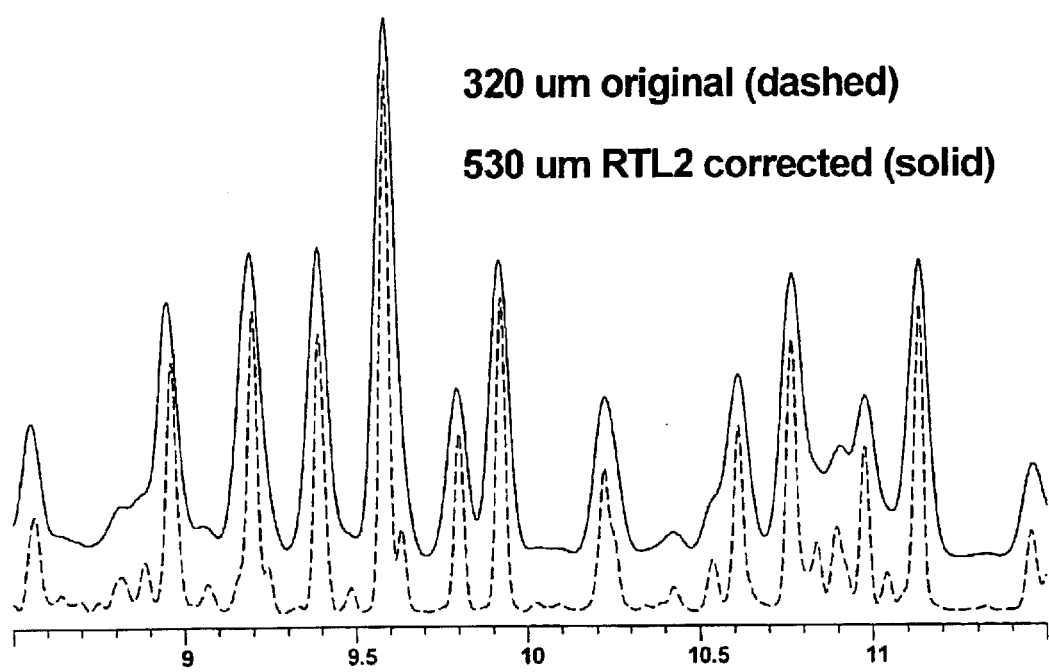
FIG. 26 shows an expanded view of reference and corrected local orange oil chromatograms.

FIG. 25 shows the two original chromatograms and the corrected 530 chromatogram for comparison. FIG. 26 shows an expanded view of the 320 chromatogram and the corrected 530 chromatogram. The lower resolution of the 530 corrected chromatogram reflected the reduced chromatographic resolution of the larger diameter column and conditions and is not an artifact of the RTL II method.

This example shows the utility of the RTL II method for improving graphical comparison of chromatograms.

EXAMPLE 10

Figure 27:
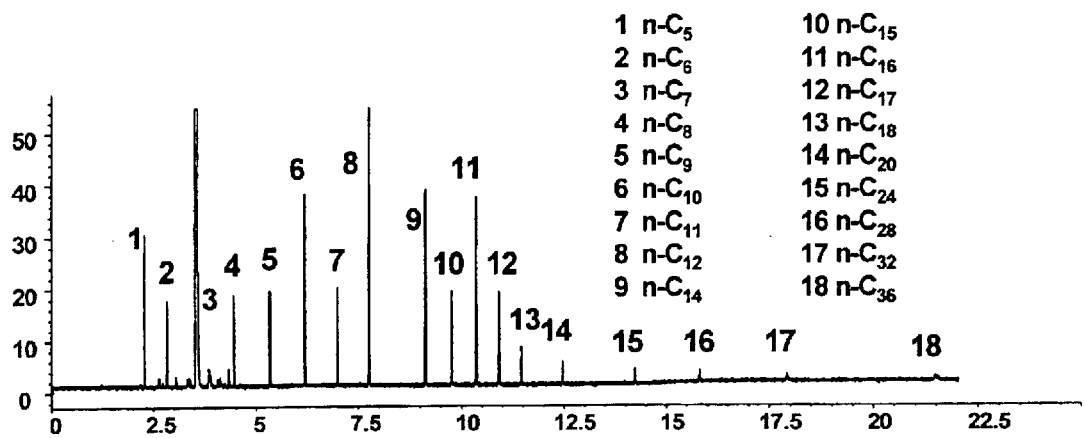
FIG. 27 depicts a reference calibration on the GC-AED system for diesel fuel analysis.

Incorporating Y-Axis Transformation of Chromatographic Data into the RTL II Method In this example, two identical GC-AED systems were set up to analyze diesel fuels. The columns were run in constant flow mode. The RT differences between the reference and local calibrations ranged from 0.003–0.300 minutes, and the RTL I was not used. The reference calibration chromatogram is shown in FIG. 27.

Figure 28:
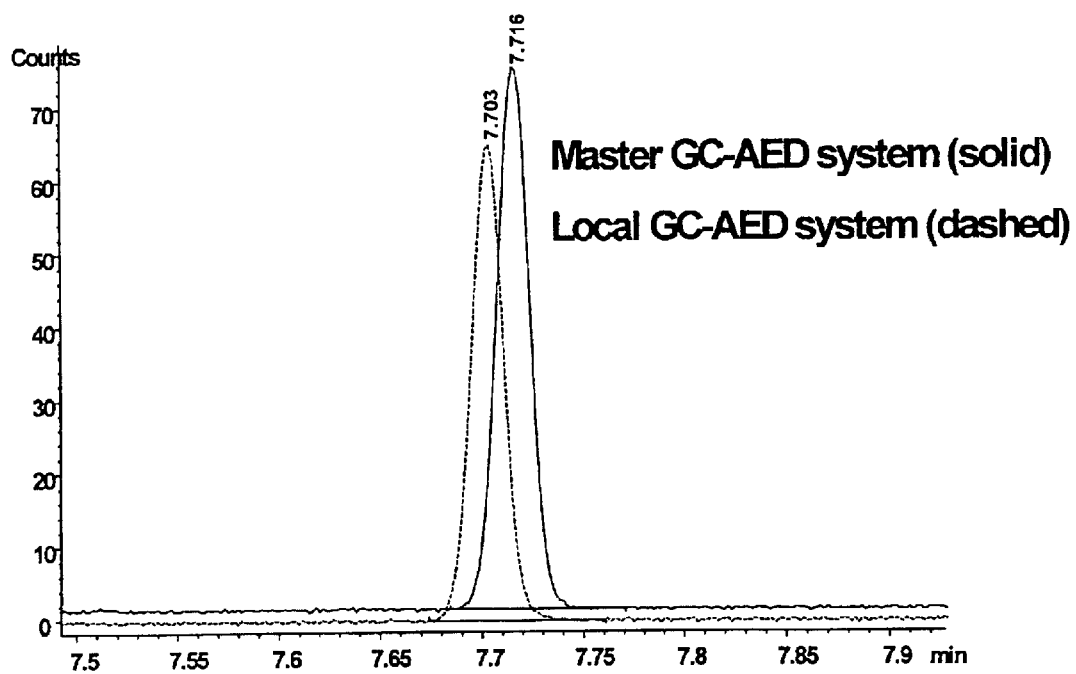
FIG. 28 shows the n-dodecane peaks from the reference and local calibrations on the GC-AED system for diesel fuel analysis.

FIG. 28 shows an expanded view of the n-dodecane peaks from the reference and local calibrations. The difference in gain and offset in the peak response (y-axis) and RT (x-axis) are clearly visible.

Figure 29:
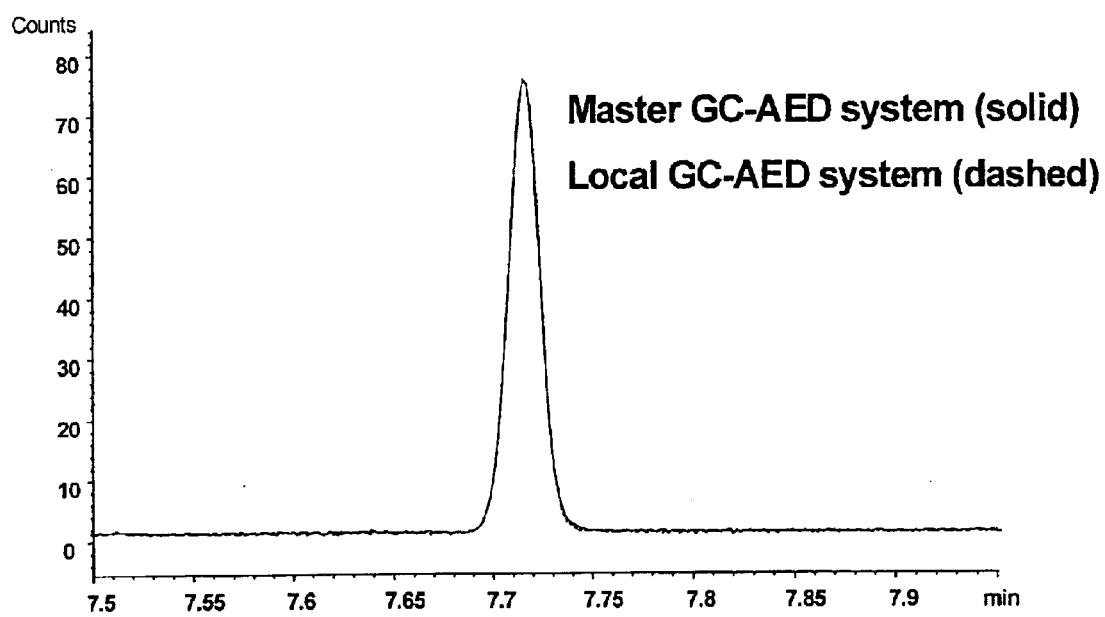
FIG. 29 shows the n-dodecane peaks from the reference and local calibrations on the GC-AED system after the RTL II transformation with linear transformation of the y-axis.

FIG. 29 shows the same peak from FIG. 28, but after the local chromatographic data has been x-axis corrected and then y-axis corrected. The two peaks now superimpose nicely.

Figure 30:
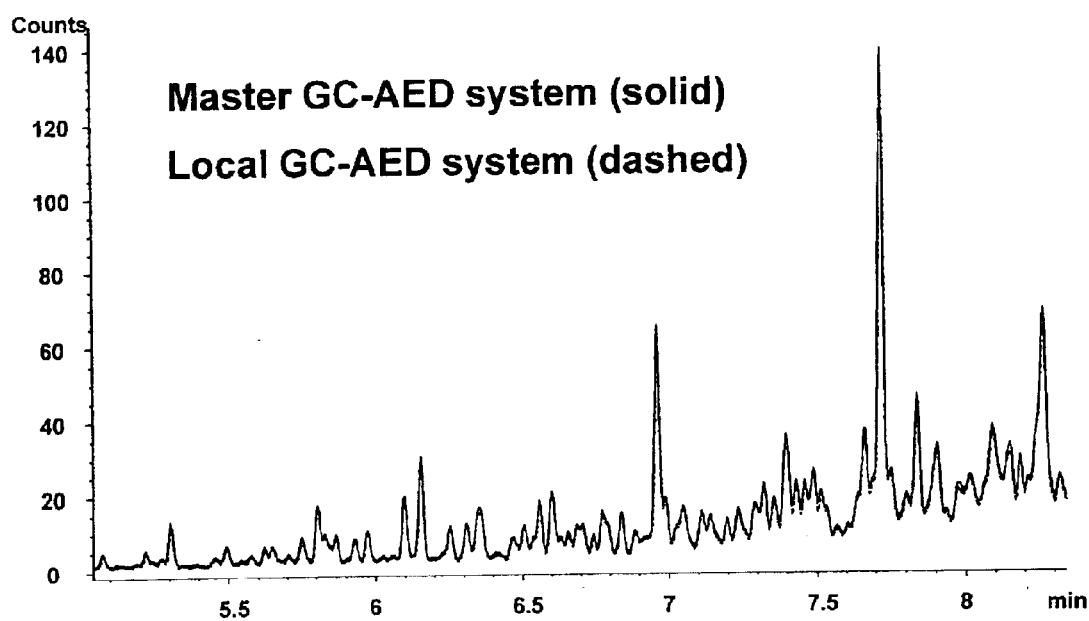
FIG. 30 shows a portion of the diesel fuel chromatograms run on the reference and local GC-AED system, with the local chromatogram being corrected in both the x and y axis.

FIG. 30 shows a portion of diesel fuel chromatograms run on the two systems. The shown chromatogram from the local AED system was corrected in both the x and y axes using RTL II. Again, the two chromatograms now superimpose very well.

EXAMPLE 11

Variant of Invention for Application to RT Libraries and Databases

Figure 31:
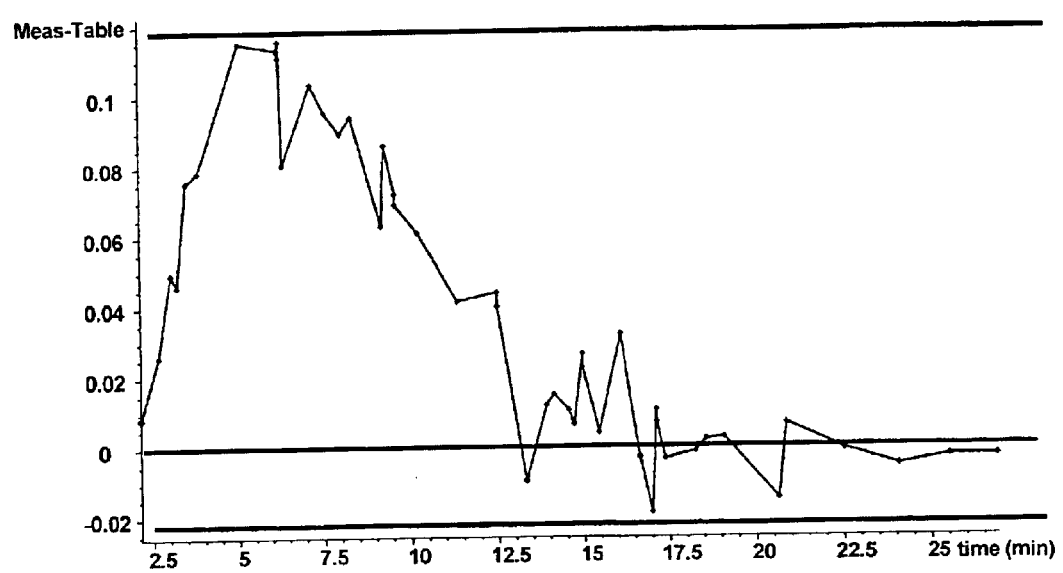
FIG. 31 shows the RT differences between local GC chromatographic data and a reference table of solvent RTs.

This example demonstrates the reduction or elimination of the difference in RTs between a local GC system and a database or library (reference system). FIG. 31 shows a plot of the difference between the measured (local) retention times as a function of run time on a local GC and those in a database of solvent retention times. The deviations from the table range from about −0.02 min to 0.12 min. This means the time window should be at least 0.15 minutes for searching unknowns against the database.

Figure 32:
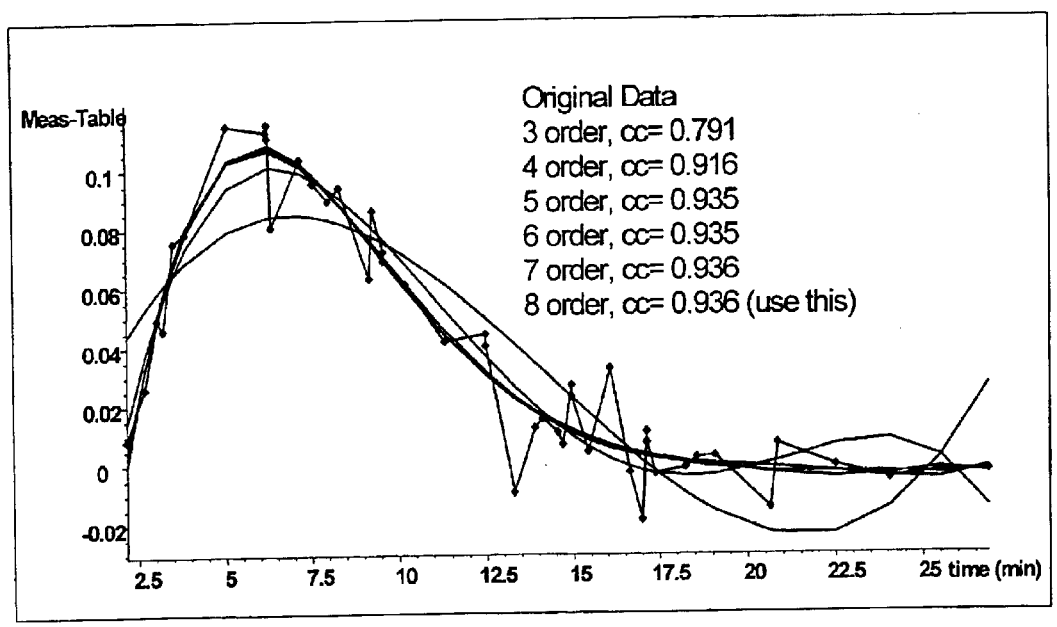
FIG. 32 depicts the results of a polynomial regression through difference data from FIG. 31, which then forms the basis of a local system calibration function.

FIG. 32 shows the third through eighth order polynomial regression results for the RT difference data. The fifth through the eighth orders all fit the difference function well. The eighth order was chosen to correct the RT table.

Figure 33:
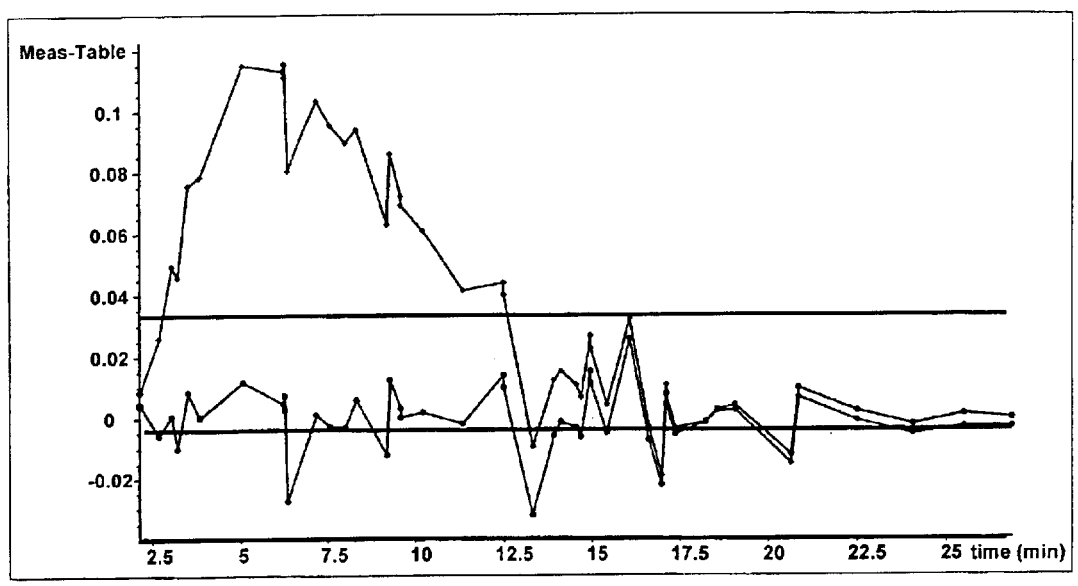
FIG. 33 shows RT differences between local chromatographic data and the reference table of solvent RTs. The top trace is before correction, the bottom trace is after correction of the table (or local data) using the local system correction function.

FIG. 33 compares the time differences between the local system and both corrected table and the original table. With the corrected table, the search time window could be reduced to about 0.05 minutes, representing nearly a threefold improvement.

Although a number of embodiments and their advantages have been described in detail, various changes, substitutions and alterations can be made herein without departing from the scope of the RTL II process as defined by the appended claims and their equivalents.

What is claimed is:

1. A process for correcting a time axis of local chromatographic data to match reference chromatographic data while maintaining peak areas, comprising:

obtaining reference calibration data from a reference chromatographic system;

obtaining local calibration data from a local chromatographic system;

generating local system correction functions based on an appropriate mathematical relationship using the reference calibration and the local calibration data; and applying the local system correction functions to local chromatographic data to generate corrected local chromatographic data, wherein the corrected local chromatographic data match with the reference calibration data on time axis and wherein peak areas in the local chromatographic data are maintained in the corrected local chromatographic data, wherein the local system correction functions include a smoothed x-axis correction function and a y-axis correction function generated using one or more mathematical curve fitting techniques, said y-axis correction function is a first derivative of the x-axis correction function.

2. The process of claim 1, wherein the one or more mathematical curve fitting techniques are selected from the group consisting of linear regression, polynomial regression, logarithmic regression, cubic splining, and exponential regression.

3. The method of claim 1, wherein the local system correction functions are applied to the local chromatographic data through steps of:

(1) determining a retention time correction ($\Delta rt$) from the smoothed x-axis correction function for a given reference retention time (rt);

(2) copying a y value that is at retention time (rt+$\Delta rt$) in the local chromatographic data to rt;

(3) multiplying copied y value by (1+d$\Delta rt$/drt), wherein d$\Delta rt$/drt is determined from the first derivative of the smoothed x-axis correction function;

repeating steps (1) to (3) with each retention time data point in the local chromatographic data to create corrected local chromatographic data.

4. The process of claim 1, further comprising:

replacing a y-axis unit in at least one of the reference calibration data and the local calibration data with a new y-axis unit.

5. The process of claim 4, wherein the new y-axis unit is concentration, percent, weight, mass, moles, or mole fraction.

6. The process of claim 1, further comprising:

applying the local system correction functions to adjust the local calibration data and to generate time-axis correct local calibration data that maintains the peak areas of the local calibration data;

determining a y-axis local response correction function using the time-axis correct local calibration data and the reference calibration data;

applying the y-axis local system response correction function to the local chromatographic data.

7. The process of claim 1, wherein generation of at least one of the local system correction functions and the corrected local chromatographic data is performed at a remote location through a network.

8. The process of claim 7, wherein the network is a local network or the Internet.

9. A process for correcting local chromatographic data with a reference retention time database, comprising:

providing a reference retention time database;

running a calibration mix on the local system to generate location calibration data;

constructing local system correction functions to minimize differences between the local calibration data and corresponding retention time values in the reference retention time database for the calibration mix;

applying the local system correction functions to adjust local chromatographic data; and using adjusted local chromatographic data to search the reference retention time database to obtain more accurate search results.

10. The process of claim 9 further comprising: locking a local system to the reference retention dine database using an instrumental method.

11. The process of claim 10, wherein the instrumental method is RTL I method.

12. A process for correcting local chromatographic data by generating a local retention time database from a reference retention time database, comprising:

providing a reference retention time database;

locking a local system to the reference retention time database using an instrumental method;

running a calibration mix on the local system to generate local calibration data;

constructing local system correction functions to minimize differences between the local calibration data and corresponding retention time values in the reference retention time database for the calibration mix;

applying the local system correction functions to adjust the reference retention time database values to generate a local retention time database; and searching the local retention time database using local chromatographic data.

13. A chromatographic apparatus for analyzing samples, comprising:

means for producing local chromatographic data; and means for generating corrected local chromatographic data that match with reference chromatographic data on a time axis while maintaining peak areas of the local chromatographic data, further comprising:

means for creating local system correction functions based on an appropriate mathematical relationship using reference calibration data local calibration data;

means for applying the local system correction functions to local chromatographic data;

means for replacing a y-axis unit in at least one of the reference calibration data and local calibration data with a new y-axis unit.

14. The chromatographic apparatus of claim 13, wherein the means for generating corrected local chromatographic data further comprising:

means for determining a y-axis local system response correction function; and means for applying the y-axis local system response correction function to the local chromatographic data.

* * * * *

UNITED STATES PATENT AND TRADEMARK OFFICE
CERTIFICATE OF CORRECTION

PATENT NO. : 6,915,227 B2
DATED : July 5, 2005
INVENTOR(S) : Quimby et al.

It is certified that error appears in the above-identified patent and that said Letters Patent is hereby corrected as shown below:

Column 18,
Line 57, after "9" insert -- , --.
Line 58, delete "dine" and insert -- time --, therefor.

Column 20,
Line 3, after "data" insert -- and --.
Line 6, after "data;" insert -- and --.

Signed and Sealed this

Eighth Day of November, 2005

JON W. DUDAS
*Director of the United States Patent and Trademark Office*